(12) United States Patent
Mishima

(10) Patent No.: US 11,344,191 B2
(45) Date of Patent: May 31, 2022

(54) ENDOSCOPE SYSTEM INCLUDING PROCESSOR FOR DETERMINING TYPE OF ENDOSCOPE

(71) Applicant: FUJIFILM Corporation, Tokyo (JP)

(72) Inventor: Takahiro Mishima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 92 days.

(21) Appl. No.: 16/748,904

(22) Filed: Jan. 22, 2020

(65) Prior Publication Data

US 2020/0237201 A1 Jul. 30, 2020

(30) Foreign Application Priority Data

Jan. 24, 2019 (JP) .............................. JP2019-009945

(51) Int. Cl.
*A61B 1/06* (2006.01)
*A61B 1/00* (2006.01)
*A61B 1/05* (2006.01)
*A61B 1/12* (2006.01)

(52) U.S. Cl.
CPC ........ *A61B 1/0638* (2013.01); *A61B 1/00006* (2013.01); *A61B 1/00009* (2013.01); *A61B 1/00059* (2013.01); *A61B 1/05* (2013.01); *A61B 1/128* (2013.01)

(58) Field of Classification Search
CPC ............ A61B 1/00006; A61B 1/00009; A61B 1/00059; A61B 1/0638; A61B 1/128; A61B 1/00062; H04N 5/243
See application file for complete search history.

(56) References Cited

U.S. PATENT DOCUMENTS

| 4,884,133 | A  | * | 11/1989 | Kanno |
| 4,951,135 | A  | * | 8/1990 | Sasagawa |
| 10,349,027 | B2 |   | 7/2019 | Tanaka et al. |
| 2002/0177751 | A1 | * | 11/2002 | Ueno |
| 2003/0063188 | A1 | * | 4/2003 | Takahashi |
| 2004/0143157 | A1 | * | 7/2004 | Doguchi |
| 2007/0100202 | A1 | * | 5/2007 | Murata |
| 2008/0074492 | A1 | * | 3/2008 | Iwasaki |

(Continued)

FOREIGN PATENT DOCUMENTS

| JP | 2011-036361 A | 2/2011 |
| JP | 2015-066049 A | 4/2015 |

(Continued)

OTHER PUBLICATIONS

An Office Action; "Notice of Reasons for Refusal", mailed by the Japanese Patent Office dated Jan. 5, 2022, which corresponds to Japanese Patent Application No. 2019-009945 and is related to U.S. Appl. No. 16/748,904; with English language translation.

*Primary Examiner* — Michael J Carey
*Assistant Examiner* — Stephen Floyd London
(74) *Attorney, Agent, or Firm* — Studebaker & Brackett PC

(57) ABSTRACT

A type acquisition unit determines the type of an endoscope connected to an endoscope connection unit. A light source control unit performs control to make the light emission balance of light in the respective wavelength ranges, which is obtained in a case where the type of the endoscope corresponds to a first endoscope, and the light emission balance of light in the respective wavelength ranges, which is obtained in a case where the type of the endoscope corresponds to a second endoscope, be different from each other.

7 Claims, 14 Drawing Sheets

(56) References Cited

U.S. PATENT DOCUMENTS

| | | | |
|---|---|---|---|
| 2008/0255411 A1* | 10/2008 | Kobayashi | |
| 2011/0034770 A1* | 2/2011 | Endo | |
| 2011/0069199 A1* | 3/2011 | Yamazaki | |
| 2013/0041220 A1* | 2/2013 | Kutsuma | |
| 2015/0091447 A1* | 4/2015 | Kubo | |
| 2015/0092032 A1* | 4/2015 | Kuramoto | G02B 23/2469 348/68 |
| 2016/0022126 A1 | 1/2016 | Ramesh et al. | |
| 2016/0235285 A1 | 8/2016 | Shirota et al. | |
| 2017/0020378 A1 | 1/2017 | Godo | |
| 2017/0273541 A1* | 9/2017 | Watanabe | |
| 2017/0296037 A1* | 10/2017 | Yoshino | |
| 2017/0332889 A1* | 11/2017 | Akiba | |
| 2019/0064499 A1* | 2/2019 | Ogawa | |
| 2019/0082929 A1* | 3/2019 | Watanabe | |
| 2019/0117041 A1* | 4/2019 | Tanaka | |
| 2020/0060530 A1* | 2/2020 | Yabe | |

FOREIGN PATENT DOCUMENTS

| | | |
|---|---|---|
| JP | 6049945 B2 | 12/2016 |
| JP | 6086602 B2 | 3/2017 |
| WO | 2015/064470 A1 | 5/2015 |
| WO | 2015/174146 A1 | 11/2015 |
| WO | 2018/061291 A1 | 4/2018 |
| WO | 2018/198507 A1 | 11/2018 |

* cited by examiner

ENDOSCOPE SYSTEM INCLUDING PROCESSOR FOR DETERMINING TYPE OF ENDOSCOPE

CROSS-REFERENCE TO RELATED APPLICATIONS

This application claims priority under 35 U.S.C. § 119(a) to Japanese Patent Application No. 2019-009945 filed on Jan. 24, 2019. The above application is hereby expressly incorporated by reference, in its entirety, into the present application.

BACKGROUND OF THE INVENTION

1. Field of the Invention

The present invention relates to an endoscope system that uses light in a plurality of wavelength ranges.

2. Description of the Related Art

In recent years, an endoscope system comprising a light source device, an endoscope, and a processor device has been widely used in a medical field. In the endoscope system, illumination light is applied to an object to be observed from a distal end part of the endoscope, and the image of the object to be observed is displayed on a monitor on the basis of RGB image signals that are obtained in a case where the image of the object to be observed, which is being illuminated with the illumination light, is picked by an image pickup element of the endoscope.

Further, as disclosed in JP6086602B and JP6049945B (corresponding to U.S. Ser. No. 10/349,027B2), light, which is a combination of pieces of light in a plurality of wavelength ranges, such as blue light, green light, and red light, has been used as illumination light in recent years. In JP6086602B, for the suppression of the generation of heat from a distal end part of an endoscope, the temperature of the distal end part of the endoscope is monitored by a temperature sensor provided in the distal end part of the endoscope and the amounts of one or more pieces of light of the pieces of light in a plurality of wavelength ranges are reduced in a case where the temperature of the distal end part is equal to or higher than a specific temperature. Further, in JP6049945B, the light emission ratio of only light having an interested color among pieces of light having a plurality of colors is raised to adjust light emission balance, so that an unnecessary increase in the amount of generated heat, which is caused by an increase in the amounts of the other pieces of light except for the light having the interested color, is suppressed.

SUMMARY OF THE INVENTION

In recent years, different types of endoscopes have been used depending on the purpose of diagnosis. Examples of the type of an endoscope include a small-diameter endoscope and a large-diameter endoscope that are different from each other in the diameter of a distal end part, a magnifying endoscope that is provided with a magnification optical system used to magnify or reduce an object to be observed in size, and a non-magnifying endoscope that is not provided with a magnification optical system. Even in a case where the types of endoscopes are different from each other as described above, there is a demand that an object is observed in a state where the generation of heat from the distal end parts of the endoscopes is suppressed. However, JP6086602B and JP6049945B do not disclose and suggest a technique that can suppress the generation of heat from a distal end part of an endoscope and can ensure brightness to the maximum according to the type of the endoscope.

An object of the invention is to provide an endoscope system that can allow a user to observe an object in a state where the generation of heat from a distal end part of an endoscope is suppressed according to the type of the endoscope in a case where the object is illuminated with a combination of pieces of light in a plurality of wavelength ranges.

An endoscope system according to an aspect of the invention comprises a light source unit that emits light in a plurality of wavelength ranges and is capable of changing a light emission ratio of the light in the respective wavelength ranges, an endoscope that includes an image pickup sensor picking up an image of an object to be observed illuminated with the light in the respective wavelength ranges, an image acquisition unit that acquires image signals obtained from the image pickup of the object to be observed, a type acquisition unit that determines a type of the endoscope connected to an endoscope connection unit, and a light source control unit that controls the light source unit to control light emission balance of the light in the respective wavelength ranges. The light source control unit performs control to make the light emission balance, which is obtained in a case where the type of the endoscope corresponds to a first endoscope, and the light emission balance, which is obtained in a case where the type of the endoscope corresponds to a second endoscope, be different from each other.

The light in the respective wavelength ranges includes light in a short wavelength range, green light, or red light; a normal light observation mode and a special light observation mode, which are different from each other in the light emission balance, are provided; and the light source control unit performs at least any one of making a light emission ratio of the light in the short wavelength range or the red light, which is obtained in a case where the type of the endoscope corresponds to the first endoscope, be higher than a light emission ratio of the light in the short wavelength range or the red light, which is obtained in a case where the type of the endoscope corresponds to the second endoscope, in the normal light observation mode, or making a light emission ratio of the green light or the red light, which is obtained in a case where the type of the endoscope corresponds to the first endoscope, be higher than a light emission ratio of the green light or the red light, which is obtained in a case where the type of the endoscope corresponds to the second endoscope, in the special light observation mode.

It is preferable that the endoscope system further comprises a general control unit controlling at least any one of the control performed by the light source control unit, image pickup control of the image pickup sensor, or processing to be performed on the image signals. It is preferable that the general control unit reduces amounts of emitted light in the respective wavelength ranges and performs brightness adjustment processing A, which is used in a case where the amounts of emitted light are reduced, on pixels of the image pickup sensor or the image signals in a case where the type of the endoscope corresponds to the first endoscope, cumulative light emission time, which is determined on the basis of the amounts of emitted light in the respective wavelength ranges and time having passed from a start of emission of the light in the respective wavelength ranges, exceeds a threshold value for light emission, and the amount of emitted light in at least one wavelength range of the light in the respective wavelength ranges exceeds a limited amount of emitted light. It is preferable that the brightness adjustment processing A increases brightness according to a reduction in the amount of emitted light.

It is preferable that the general control unit maintains the amounts of emitted light in the respective wavelength ranges and performs brightness adjustment processing B, which is used in a case where the amount of emitted light is maintained, on pixels of the image pickup sensor or the image signal in a case where the type of the endoscope corresponds to the second endoscope and the amount of emitted light in at least one wavelength range of the light in the respective wavelength ranges reaches a limited amount of emitted light.

It is preferable that the limited amount of emitted light is determined on the basis of a gain-up upper limit for gain processing for brightness adjustment processing A in a case where the brightness adjustment processing A is the gain processing for brightness adjustment processing A. It is preferable that the limited amount of emitted light is determined on the basis of a gain-up upper limit for gain processing for brightness adjustment processing B in a case where the brightness adjustment processing B is the gain processing for brightness adjustment processing B.

It is preferable that a diameter of a distal end part of the first endoscope is larger than a diameter of a distal end part of the second endoscope. It is preferable that the first endoscope is a magnifying endoscope and the second endoscope is a non-magnifying endoscope.

According to the invention, it is possible to observe an object in a state where the generation of heat from a distal end part of an endoscope is suppressed according to the type of the endoscope in a case where the object is illuminated with a combination of pieces of light in a plurality of wavelength ranges.

Figure 12:
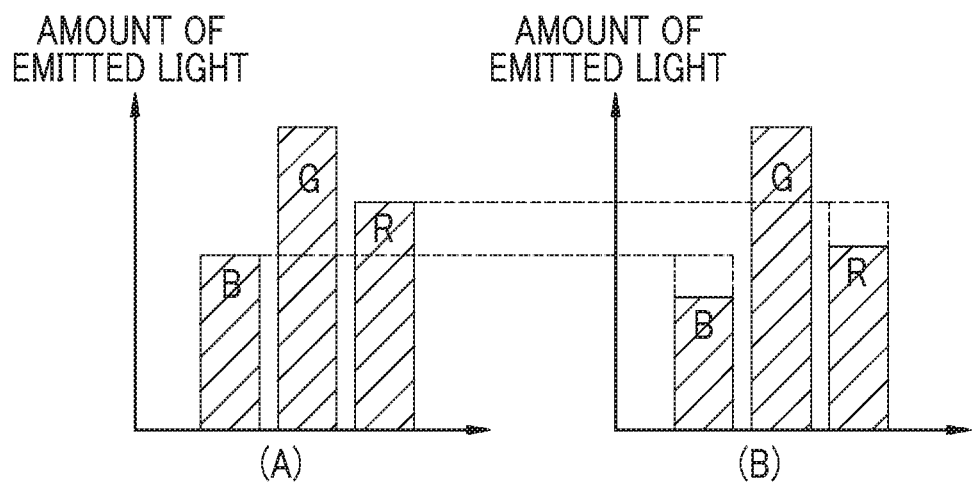

(A) of FIG. 12 is a diagram illustrating the light emission balance of normal light in a case where a first endoscope is connected and (B) of FIG. 12 is a diagram illustrating the light emission balance of normal light in a case where a second endoscope is connected.

Figure 13:
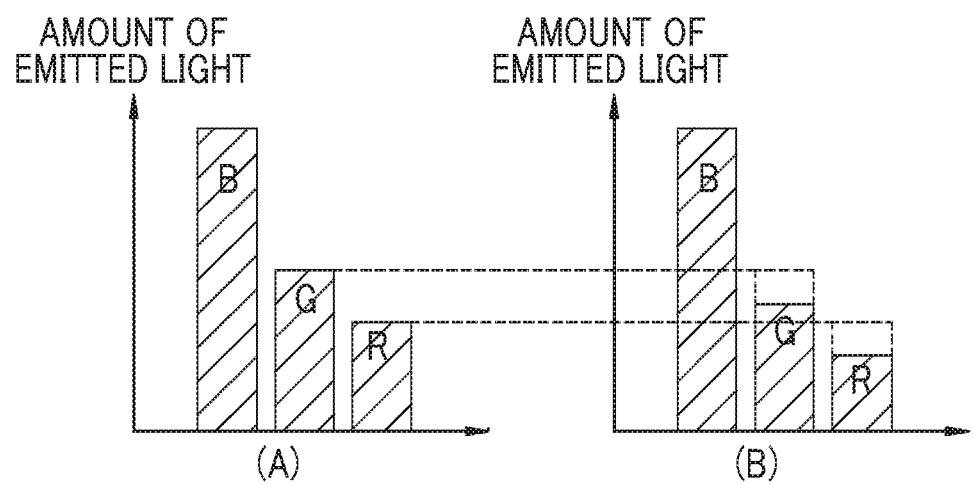

(A) of FIG. 13 is a diagram illustrating the light emission balance of special light in a case where the first endoscope is connected and (B) of FIG. 13 is a diagram illustrating the light emission balance of special light in a case where the second endoscope is connected.

Figure 14:
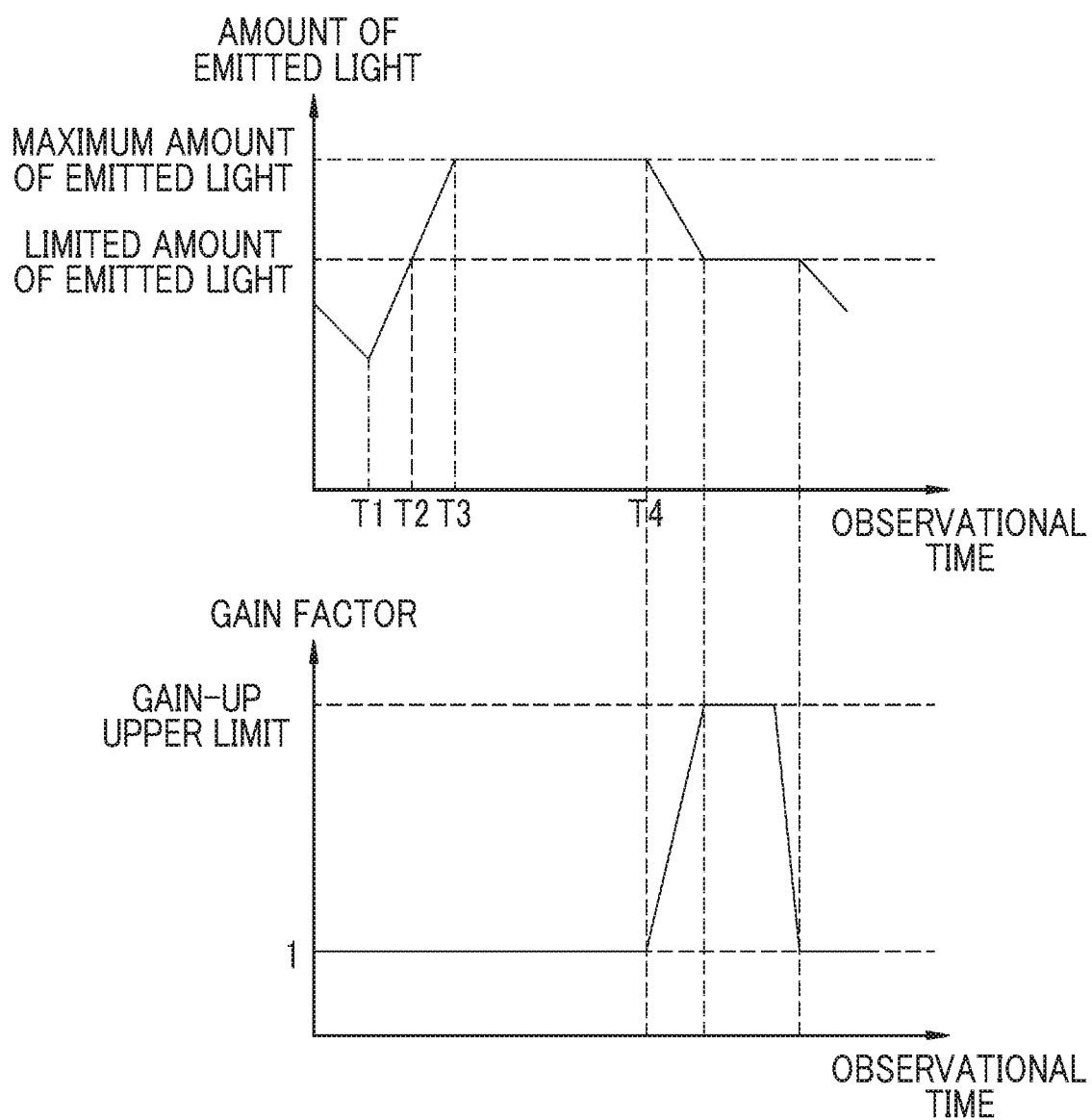

FIG. 14 is a graph showing a relationship between the amount of emitted light and a gain factor in a case where the first endoscope is connected.

Figure 15:
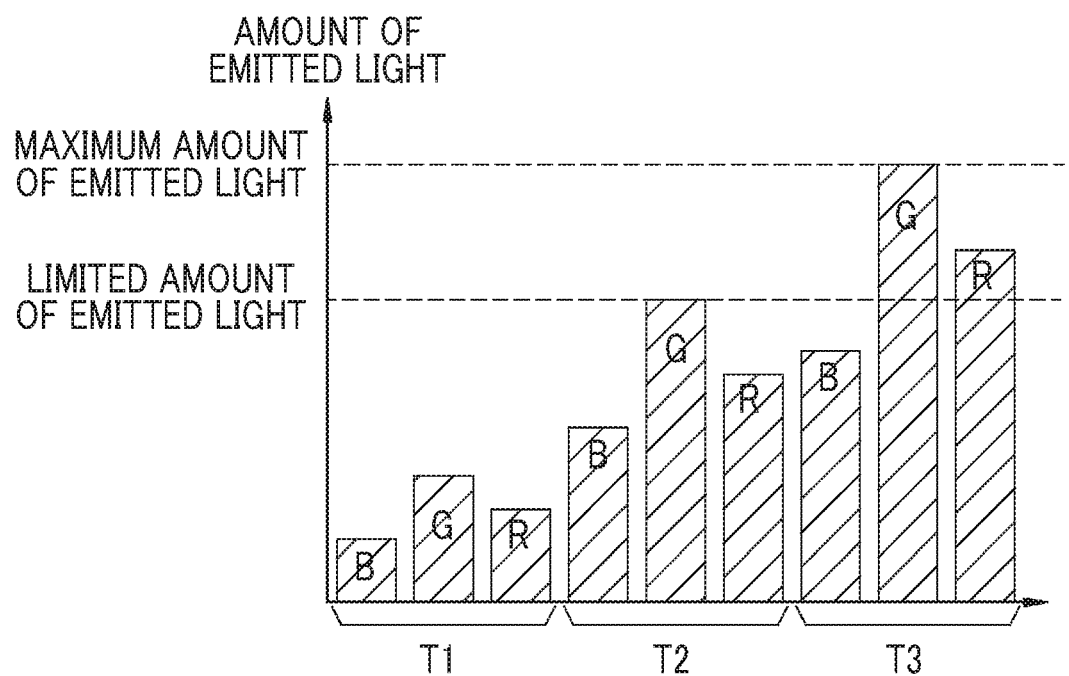

FIG. 15 is a graph showing the amounts of normal light emitted at timings T1, T2, and T3 in a case where the first endoscope is connected.

Figure 16:
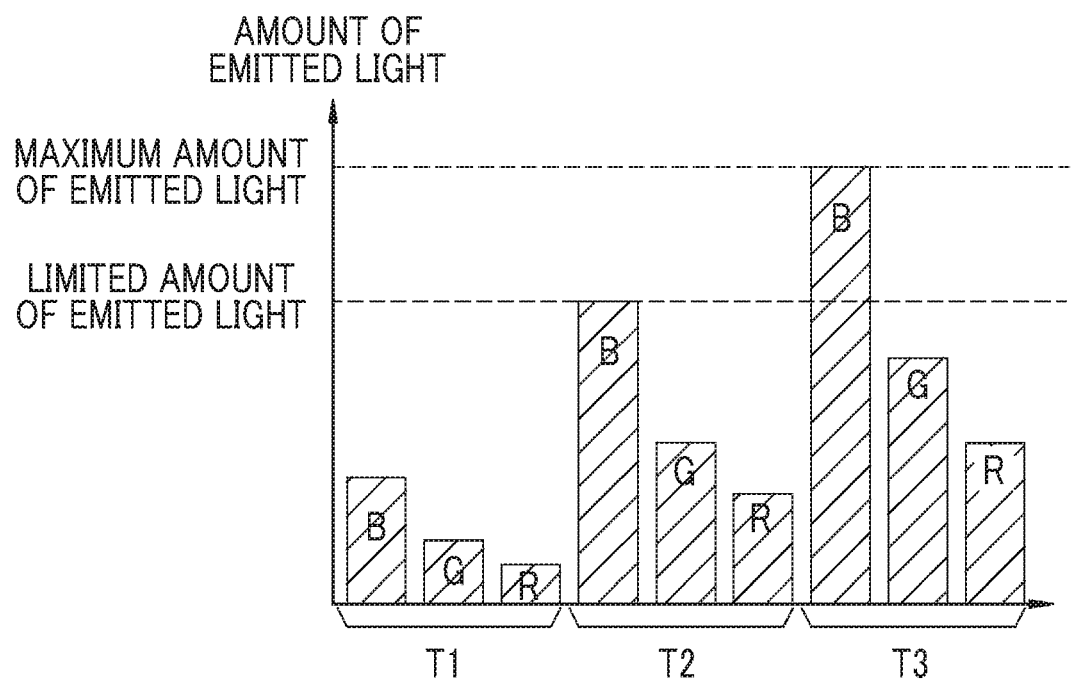

FIG. 16 is a graph showing the amounts of special light emitted at timings T1, T2, and T3 in a case where the first endoscope is connected.

Figure 17:
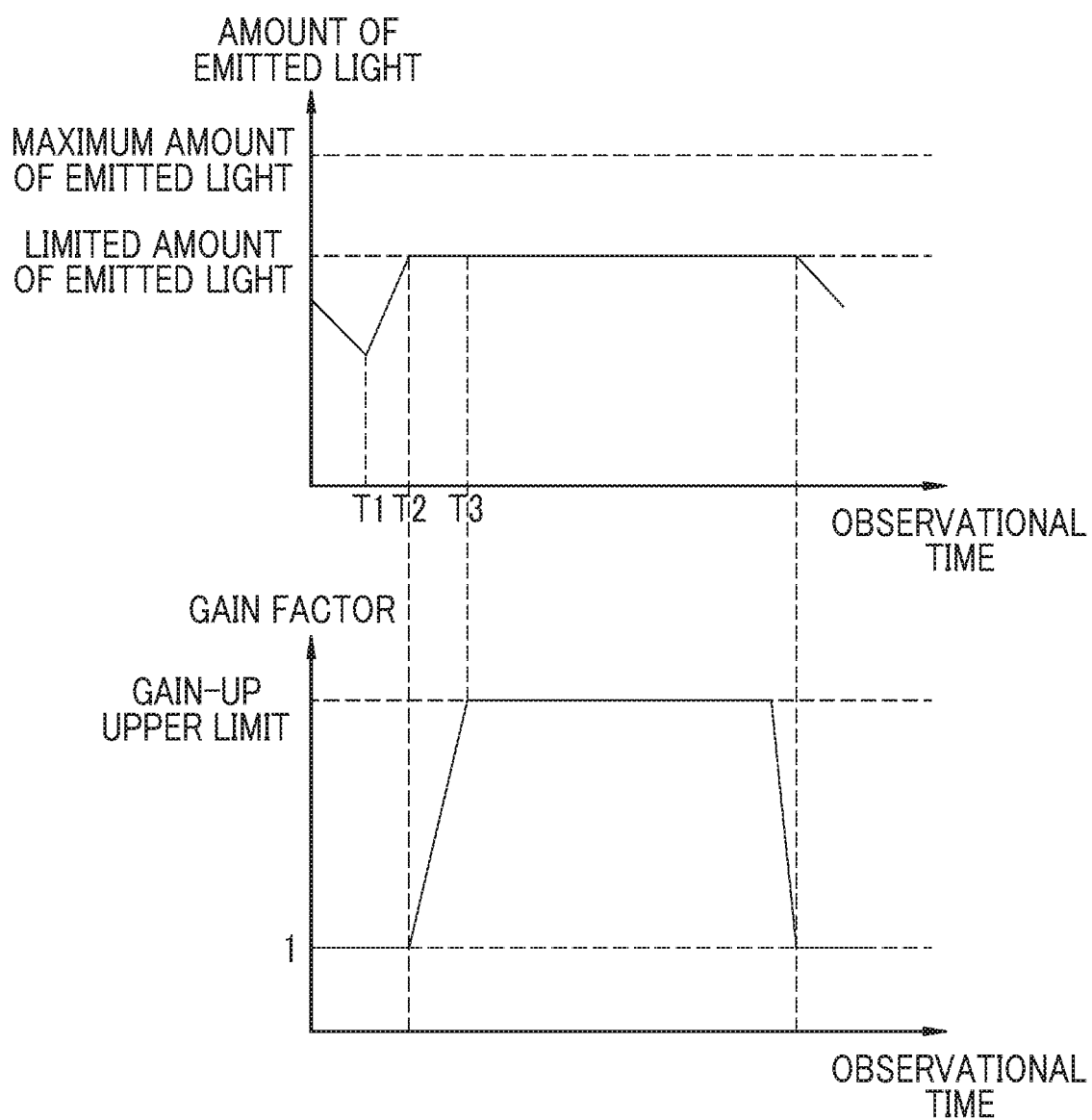

FIG. 17 is a graph showing a relationship between the amount of emitted light and a gain factor in a case where the second endoscope is connected.

Figure 18:
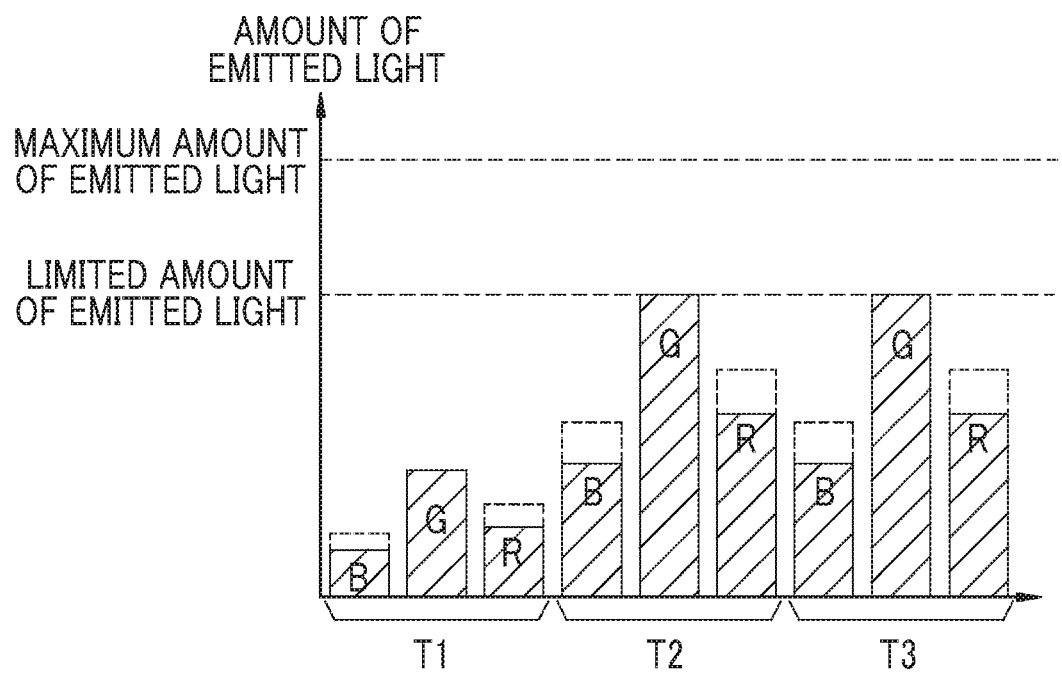

FIG. 18 is a graph showing the amounts of normal light emitted at timings T1, T2, and T3 in a case where the second endoscope is connected.

Figure 19:
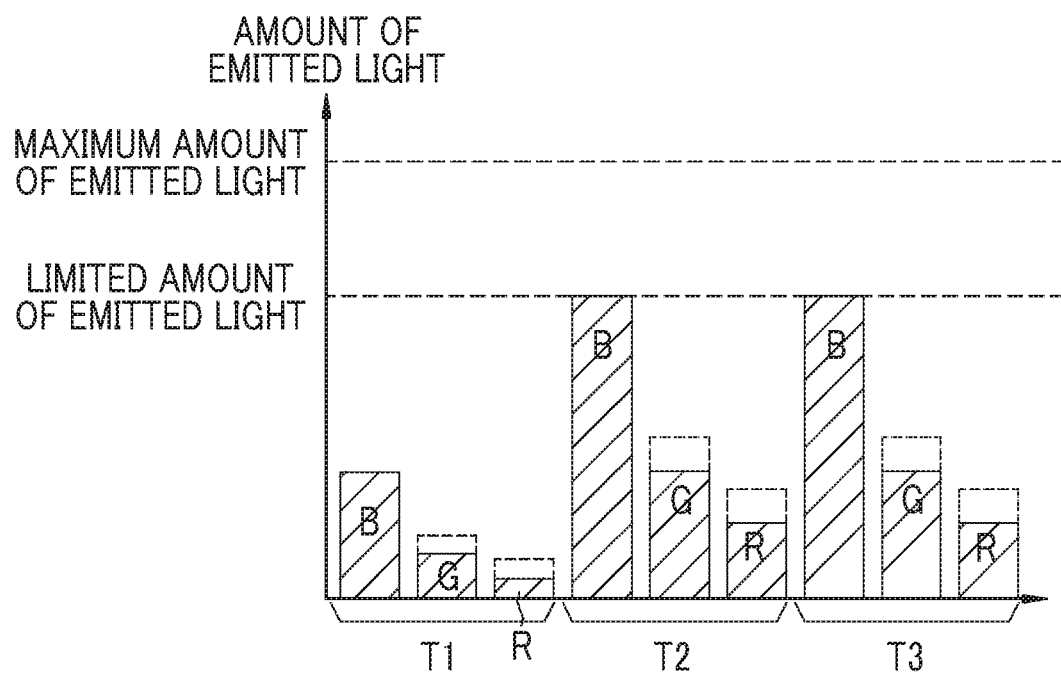

FIG. 19 is a graph showing the amounts of special light emitted at timings T1, T2, and T3 in a case where the second endoscope is connected.

DESCRIPTION OF THE PREFERRED EMBODIMENTS

First Embodiment

Figure 1:
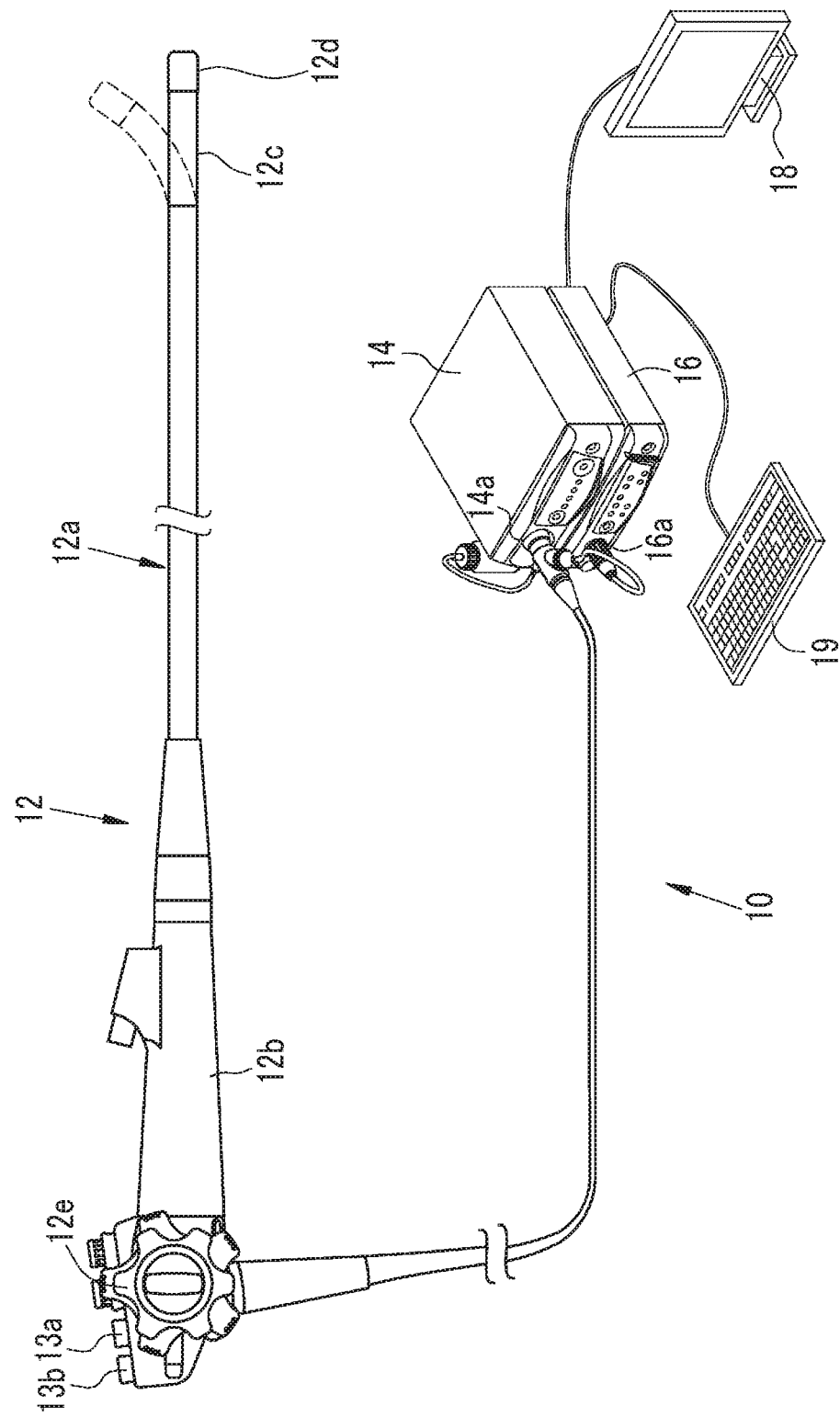
FIG. 1 is a diagram showing the appearance of an endoscope system according to a first embodiment.

As shown in FIG. 1, an endoscope system 10 according to a first embodiment includes an endoscope 12, a light source device 14, a processor device 16, a monitor 18 (display unit), and a user interface 19. The endoscope 12 is optically connected to a light source-side connection unit 14a of the light source device 14, and is electrically connected to a processor-side connection unit 16a of the processor device 16. The light source-side connection unit 14a and the processor-side connection unit 16a form an endoscope connection unit to which the endoscope 12 is to be connected. The endoscope 12 includes an insertion part 12a that is to be inserted into an object to be examined, an operation part 12b that is provided at the proximal end portion of the insertion part 12a, a bendable part 12c that is provided on the distal end side of the insertion part 12a, and a distal end part 12d. In a case where angle knobs 12e of the operation part 12b are operated, the bendable part 12c is operated to be bent. As the bendable part 12c is operated to be bent, the distal end part 12d faces in a desired direction. The user interface 19 includes a mouse and the like in addition to a keyboard shown in FIG. 1.

Further, the operation part 12b is provided with, for example, a mode changeover switch 13a and a static image-acquisition instruction unit 13b in addition to the angle knobs 12e. The mode changeover switch 13a is used for an operation for switching a normal light observation mode and a special light observation mode. The normal light observation mode is a mode where a normal observation image is displayed on the monitor 18. The special light observation mode is a mode where a special observation image is displayed on the monitor 18. A foot switch may be used as a mode switching unit, which is used to switch a mode, other than the mode changeover switch 13a.

The processor device 16 is electrically connected to the monitor 18 and the user interface 19. The monitor 18 outputs and displays image information and the like. The user interface 19 functions as a user interface (UI) that receives an input operation, such as function settings. For example, in a case where an image quality mode of a normal observation image or a special observation image is to be set, a user may operate the user interface 19 to display an image quality setting screen and to select an image quality mode from the image quality setting screen. An external recording unit (not shown), which records image information and the like, may be connected to the processor device 16.

IQLabel is used as a parameter based on an image quality mode. IQLabel is set to a value that is larger than "0" and equal to or smaller than "1", and a larger value is used as IQLabel as an image quality mode is higher. Two stages of a high image quality mode and a low image quality mode are used as an image quality mode in this embodiment, but three or more image quality modes may be used. IQLabel of the high image quality mode is set to "1" and IQLabel of the low image quality mode is set to a value smaller than "1". The details of a method of using IQLabel will be described later. An image quality mode may be switched by the mode changeover switch 13a.

Figure 2:
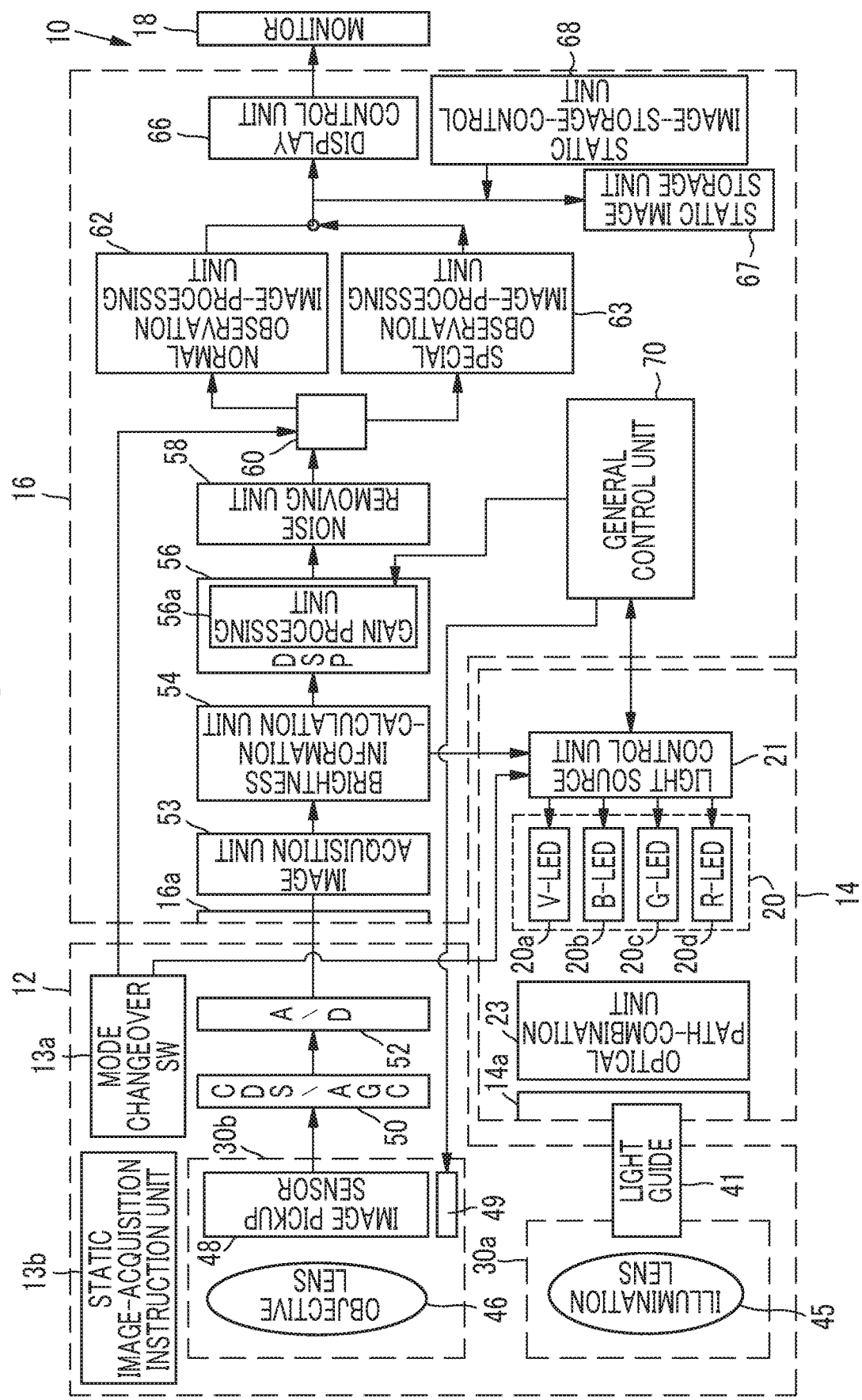
FIG. 2 is a block diagram showing the functions of the endoscope system according to the first embodiment.

As shown in FIG. 2, the light source device 14 includes a light source unit 20, a light source control unit 21, and an optical path-combination unit 23. The light source unit 20 can emit light in a plurality of wavelength ranges, and can change the light emission ratio of light in each wavelength range. The light source unit 20 emits light in four wavelength ranges of a violet-light wavelength range, a blue-light wavelength range, a green-light wavelength range, and a red-light wavelength range. Specifically, the light source unit 20 includes a violet light emitting diode (V-LED) 20a, a blue light emitting diode (B-LED) 20b, a green light emitting diode (G-LED) 20c, and a red light emitting diode (R-LED) 20d to emit light in the four wavelength ranges. The light source control unit 21 controls the drive of the LEDs 20a to 20d. The optical path-combination unit 23 combines the optical paths of pieces of light that are emitted from the four color LEDs 20a to 20d and have four colors. The pieces of light, which are combined by the optical path-combination unit 23, are applied to the inside of an object to be examined through a light guide 41, which is inserted into the insertion part 12a, and an illumination lens 45. A laser diode (LD) may be used instead of the LED.

Figure 3:
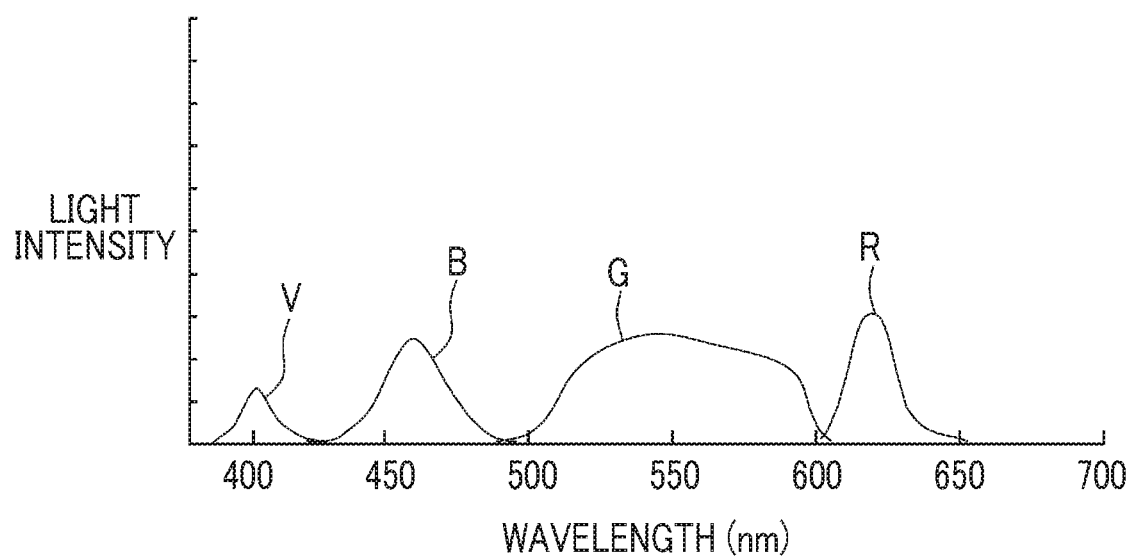
FIG. 3 is a graph showing the light emission spectra of violet light V, blue light B, green light G, and red light R.

As shown in FIG. 3, the V-LED 20a generates violet light V of which the central wavelength is in the range of 405±10 nm and the wavelength range is in the range of 380 to 420 nm. The B-LED 20b generates blue light B of which the central wavelength is in the range of 460±10 nm and the wavelength range is in the range of 420 to 500 nm. The G-LED 20c generates green light G of which the wavelength range is in the range of 480 to 600 nm. The R-LED 20d generates red light R of which the central wavelength is in the range of 620 to 630 nm and the wavelength range is in the range of 600 to 650 nm. "Light in a short wavelength range" in the invention corresponds to violet light V or blue light B, and corresponds to light including violet light V and blue light B.

The light source control unit 21 controls the light source unit 20 to control the light emission balance of the pieces of light in the respective wavelength ranges. Specifically, the light source control unit 21 controls the V-LED 20a, the B-LED 20b, the G-LED 20c, and the R-LED 20d to control the light emission balance of violet light V, blue light B, green light G, and red light R. The light emission balance of light in the normal light observation mode is different from that in the special light observation mode. Light, which is emitted with the light emission balance of light in the normal light observation mode, is referred to as normal light and light, which is emitted with the light emission balance of light in the special light observation mode, is referred to as special light. The details of the control of the light emission balance will be described later. Further, the light source control unit 21 controls the amount of illumination light, which is emitted from each of the LEDs 20a to 20d, on the basis of brightness information that is sent from a brightness information-calculation unit 54 of the processor device 16.

As shown in FIG. 2, the light guide 41 is built in the endoscope 12 and a universal cord (a cord connecting the endoscope 12 to the light source device 14 and the processor device 16), and transmits the pieces of light, which are combined by the optical path-combination unit 23, to the distal end part 12d of the endoscope 12. A multimode fiber can be used as the light guide 41. For example, a thin fiber cable of which a total diameter of a core diameter of 105 μm, a cladding diameter of 125 μm, and a protective layer forming a covering is in the range of tp 0.3 to 0.5 mm can be used.

The distal end part 12d of the endoscope 12 is provided with an illumination optical system 30a and an image pickup optical system 30b. The illumination optical system 30a includes an illumination lens 45, and light transmitted from the light guide 41 is applied to an object to be observed through the illumination lens 45. The image pickup optical system 30b includes an objective lens 46 and an image pickup sensor 48. Light reflected from the object to be observed is incident on the image pickup sensor 48 through the objective lens 46. Accordingly, the reflected image of the object to be observed is formed on the image pickup sensor 48. The image pickup control of the image pickup sensor 48 is performed by an image pickup control unit 49.

The image pickup sensor 48 is a color image pickup sensor, and picks up the reflected image of an object to be examined and outputs image signals. It is preferable that the image pickup sensor 48 is a charge coupled device (CCD) image pickup sensor, a complementary metal-oxide semiconductor (CMOS) image pickup sensor, or the like. The image pickup sensor 48 used in the invention is a color image pickup sensor that is used to obtain RGB image signals corresponding to three colors of R (red), G (green), and B (blue), that is, a so-called RGB image pickup sensor that comprises R-pixels provided with R-filters, G-pixels provided with G-filters, and B-pixels provided with B-filters.

The image pickup sensor 48 may be a so-called complementary image pickup sensor, which comprises complementary filters corresponding to C (cyan), M (magenta), Y (yellow), and G (green), instead of an RGB color image pickup sensor. In a case where a complementary image pickup sensor is used, image signals corresponding to four colors of CMYG are output. Accordingly, the image signals corresponding to four colors of CMYG need to be converted into image signals corresponding to three colors of RGB by complementary color-primary color conversion. Further, the image pickup sensor 48 may be a monochrome image pickup sensor that includes no color filter. In this case, since the light source control unit 21 causes blue light B, green light G, and red light R to be emitted in a time-sharing manner, demosaicing needs to be added to the processing of image pickup signals.

The image signals output from the image pickup sensor 48 are transmitted to a CDS/AGC circuit 50. The CDS/AGC circuit 50 performs correlated double sampling (CDS) or auto gain control (AGC) on the image signals that are analog signals. The image signals, which have been transmitted through the CDS/AGC circuit 50, are converted into digital image signals by an analog/digital converter (A/D converter) 52. The digital image signals, which have been subjected to A/D conversion, are input to the processor device 16.

The processor device 16 comprises an image acquisition unit 53, a brightness information-calculation unit 54, a digital signal processor (DSP) 56, a noise removing unit 58, a signal switching unit 60, a normal observation image-processing unit 62, a special observation image-processing unit 63, a display control unit 66, a static image storage unit 67, a static image-storage-control unit 68, and a general control unit 70.

The image acquisition unit 53 acquires image signals that are obtained in a case where the image of an object to be observed is picked up by the endoscope 12. The image signals, which are acquired by the image acquisition unit 53, are formed of red signals that are output from the R-pixels of the image pickup sensor 48, green signals that are output from the G-pixels of the image pickup sensor 48, and blue signals that are output from the B-pixels of the image pickup sensor 48. The brightness information-calculation unit 54 calculates brightness information, which represents the brightness of the object to be observed, on the basis of the image signals that are input from the image acquisition unit 53. The calculated brightness information is sent to the light source control unit 21, and is used for the control of the amount of emitted illumination light.

The DSP 56 performs various kinds of signal processing, such as defect correction processing, offset processing, gain processing, linear matrix processing, gamma conversion processing, and demosaicing, on the received image signals. The gain processing among the various kinds of signal processing is processing that is performed by a gain processing unit 56a provided in the DSP 56 and multiplies the image signals and gain factors together and adjusts the pixel values of the image signals to adjust the brightness of a normal observation image or a special observation image. With regard to the gain processing, different gain processing is performed before and after the change of the light emission balance of normal light or special light. The details of the gain processing will be described later. The noise removing unit 58 performs noise removal processing (for example, a moving-average method, median filtering, or the like) on the image signals, which have been subjected to various kinds of signal processing by the DSP 56, to remove noise from the image signals. The image signals from which noise has been removed are transmitted to the signal switching unit 60.

In a case where an observation mode is set to the normal light observation mode by the mode changeover switch 13a, the signal switching unit 60 transmits the image signals, which are obtained from illumination using normal light and image pickup, to the normal observation image-processing unit 62. Further, in a case where an observation mode is set to the special light observation mode, the signal switching unit 60 transmits the image signals, which are obtained from illumination using special light and image pickup, to the special observation image-processing unit 63.

The normal observation image-processing unit 62 performs image processing for a normal observation image on normal image signals that are obtained in the normal light observation mode. The image processing for a normal observation image includes chroma emphasis processing, color emphasis processing, and structure emphasis processing for a normal observation image, and the like. The image signals, which have been subjected to the image processing for a normal observation image, are input to the display control unit 66 from the normal observation image-processing unit 62 as a normal observation image.

The special observation image-processing unit 63 performs image processing for a special observation image on special image signals that are obtained in the special light observation mode. The image processing for a special observation image includes chroma emphasis processing, color emphasis processing, and structure emphasis processing for a special observation image, and the like. The image signals, which have been subjected to the image processing for a special observation image, are input to the display control unit 66 from the special observation image-processing unit 63 as a special observation image.

The display control unit 66 performs control to display the normal observation image or the special observation image, which is input from the normal observation image-processing unit 62 or the special observation image-processing unit 63, as an image that can be displayed by the monitor 18. An image corresponding to each observation mode is displayed by the control that is performed by the display control unit 66. The normal observation image is displayed on the monitor 18 in the normal light observation mode. Further, the special observation image is displayed on the monitor 18 in the special light observation mode.

The static image-storage-control unit 68 performs control to store an image, which is obtained at the timing of a static image-acquisition instruction, in the static image storage unit 67 as a static image according to the instruction of the static image-acquisition instruction unit 13b. In the normal light observation mode, the static image-storage-control unit 68 stores a normal observation image, which is obtained at the timing of a static image-acquisition instruction, in the static image storage unit 67 as a static image. In the special light observation mode, the static image-storage-control unit 68 stores a special observation image, which is obtained at the timing of a static image-acquisition instruction, in the static image storage unit 67 as a static image.

The general control unit 70 controls at least any one of control to be performed by the light source control unit 21, the image pickup control of the image pickup sensor 48, or processing to be performed on image signals. Specifically, the general control unit 70 controls the light source control unit 21 to perform the control of the light emission balance of normal light or special light, or the like as the control to be performed by the light source control unit 21. Further, the general control unit 70 controls the image pickup control unit 49 to control the exposure time of the pixels of the image pickup sensor 48 and the like, as the image pickup control of the image pickup sensor 48. Furthermore, the general control unit 70 controls the gain processing unit 56a to adjust the brightness of a normal observation image or a special observation image as the processing to be performed on image signals.

The general control unit 70 performs control to make the light emission ratio of light in a specific wavelength range, which is determined for each observation mode in advance, be higher than the light emission ratios of light in the other wavelength ranges so that an object to be observed can be illuminated with an emphasized color determined in each observation mode in a state where the generation of heat from the distal end part of the endoscope is suppressed and brightness is ensured to the maximum. Specifically, it is preferable that green, which can brighten the entire object to be observed, is set as an emphasized color in the normal light observation mode. For this reason, it is preferable that green light G is set as the light in a specific wavelength range and violet light V, blue light B, and red light R are set as the light in the other wavelength ranges in the normal light observation mode. Further, it is preferable that blue, which can emphasize a portion effective in the diagnosis of a lesion part, such as superficial blood vessels, is set as an emphasized color in the special light observation mode. For this reason, it is preferable that violet light V or blue light B is set as the light in a specific wavelength range and green light G and red light R are set as the light in the other wavelength ranges in the special light observation mode.

Then, in a case where the amount of emitted light based on normal light or special light is smaller than the prescribed amount of emitted light (when the amount of emitted light based on normal light or special light is smaller than the prescribed amount of emitted light), the general control unit 70 adjusts the amount of emitted violet light V, blue light B, green light G, and red light R while maintaining set light emission balance that is light emission balance set in advance. On the other hand, in a case where the amount of emitted light based on normal light or special light is equal to or larger than the prescribed amount of emitted light (when the amount of emitted light based on normal light or special light is equal to or larger than the prescribed amount of emitted light), the general control unit 70 changes the set light emission balance to adjust the amount of emitted light based on normal light or special light and performs first brightness adjustment processing on normal image signals or special image signals. The first brightness adjustment processing is to increase brightness corresponding to light in a specific wavelength range, of which the light emission ratio has been reduced, through the change of the light emission balance of normal light or special light. The amount of emitted light based on normal light or special light means the total amount of light in the respective wavelength ranges included in normal light or special light, that is, violet light V, blue light B, green light G, and red light.

The control of light emission balance and the like in a case where the amount of emitted light is smaller than the prescribed amount of emitted light in the normal light observation mode and the special light observation mode and a case where the amount of emitted light is equal to or larger than the prescribed amount of emitted light in the normal light observation mode and the special light observation mode will be described below. In a case where the amount of emitted light is smaller than the prescribed amount of emitted light in the normal light observation mode, the general control unit 70 controls the respective LEDs 20a to 20d so that light is emitted with light emission balance where the light emission ratios of violet light V, blue light B, green light G, and red light R are Vc:Bc:Gc:Rc, as the set light emission balance. Accordingly, normal light of which the light emission balance corresponds to Vc:Bc:Gc:Rc is emitted from the light source unit 20. Then, in a case where the amount of emitted light is equal to or larger than the prescribed amount of emitted light, the general control unit 70 changes the light emission balance of normal light so that the light emission ratio Gc of green light G is higher than the light emission ratios Vc, Bc, and Rc of violet light V, blue light B, and red light R. At that time, it is preferable that the light emission ratios Vc, Bc, Gc, and Rc corresponding to the respective colors are multiplied by IQLabel determined depending on an image quality mode. For example, since IQLabel is 1 in the high image quality mode, the amount of emitted green light G is not changed. On the other hand, since IQLabel is smaller than 1 in the low image quality mode, the amount of emitted green light G is reduced.

Further, in the normal light observation mode, the general control unit 70 increases brightness, which corresponds to violet light V, blue light B, or red light of which the light emission ratio has been reduced with respect to the set light emission balance, through the change of the light emission balance of normal light by the first brightness adjustment processing. Specifically, as the first brightness adjustment processing, gain processing for first brightness adjustment is performed on the blue signals corresponding to violet light V or blue light B, green signals corresponding to green light G, and red signals corresponding to red light R among the normal image signals. In the gain processing for first brightness adjustment, as shown in Equation (1), a gain factor gainB for blue signals and a gain factor gainR for red signals are multiplied by gain correction factors kB (>1) and kRc (>1), respectively. On the other hand, a gain factor gainG for green signals is not multiplied by a gain correction factor.

$$\text{gain}G^* = \text{gain}G$$

$$\text{gain}B^* = \text{gain}B \times kB$$

$$\text{gain}R^* = \text{gain}R \times kRc \qquad \text{Equation (1)}$$

gainG*, gainB*, and gainR* denote the gain factors for green signals, blue signals, and red signals having been subjected to the gain processing for first brightness adjustment. Furthermore, it is preferable that the gain correction factor kB is determined on the basis of the amount of reduction in the light emission ratio Bc of blue light B with respect to the set light emission balance. Moreover, it is preferable that the gain correction factor kRc is determined on the basis of the amount of reduction in the light emission ratio Rc of red light R with respect to the set light emission balance.

In a case where the image pickup sensor 48 is a frame sequential sensor, processing for adjusting exposure time may be performed as the first brightness adjustment processing. In this case, it is preferable that the exposure time of B-pixels receiving violet light V or blue light B or the exposure time of R-pixels receiving red light R is made to be longer than the exposure time of G-pixels receiving green light G to compensate for a reduction in the amount of violet light V, blue light B, or red light R of which the light emission ratio has been reduced with respect to the set light emission balance in a case where light emission balance is changed in the normal light observation mode. The frame sequential sensor is, for example, a sensor that is sequentially exposed to light in the respective wavelength ranges, and it is preferable that the exposure time of the frame sequential sensor is adjusted by the adjustment of the light emission time of light in each wavelength range.

It is preferable that the first brightness adjustment processing, that is, the gain processing for first brightness adjustment in the high image quality mode is different from that in the low image quality mode. Specifically, Equation (1) is multiplied by an image quality-correction factor g(IQLabel), which is based on IQLabel determined depending on an image quality mode, and it is preferable that the image quality-correction factor g(IQLabel) in the high image quality mode is different from that in the low image quality mode (see Equation (2)). It is preferable that the image quality-correction factor g(IQLabel) is the reciprocal of IQLabel. That is, the image quality-correction factor g(IQLabel) in the high image quality mode is "1" and the image quality-correction factor g(IQLabel) in the low image quality mode is a value of "1" or more.

$$gainG^* = gainG \times g(IQLabel)$$

$$gainB^* = gainB \times kB \times g(IQLabel)$$

$$gainR^* = gainR \times kRc \times g(IQLabel) \quad \text{Equation (2)}$$

It is preferable that the gain factors gainB, gainG, and gainR are set to different values in the normal light observation mode or the special light observation mode and are set to values corresponding to the sensitivity of the image pickup sensor 48. For example, it is preferable that the gain factors gainB and gainR are set to values larger than 1 as initial values while the gain factor gainG is used as a reference in the normal light observation mode. It is preferable that the gain factor gainB is set to "1" and the gain factors gainG and gainR are set to values larger than 1 as initial values in the special light observation mode. Further, in a case where the sensitivity of the image pickup sensor 48 is low, it is preferable that values exceeding "1" are set as the gain factors gainB, gainG, and gainR in any one of the normal light observation mode or the special light observation mode. On the other hand, in a case where the sensitivity of the image pickup sensor 48 is high, it is preferable that the gain factor gainG as a reference is set to a value smaller than "1" in the normal light observation mode. It is preferable that the gain factor gainB as a reference is set to "1" in terms of ensuring brightness in the special light observation mode even in a case where the sensitivity of the image pickup sensor 48 is high.

In a case where the amount of emitted light is smaller than the prescribed amount of emitted light in the special light observation mode, the general control unit 70 controls the respective LEDs 20a to 20d so that light is emitted with light emission balance where the light emission ratios of violet light V, blue light B, green light G, and red light R are Vs:Bs:Gs:Rs as the set light emission balance. Accordingly, special light of which the light emission balance corresponds to Vs:Bs:Gs:Rs is emitted from the light source unit 20. Then, in a case where the amount of emitted light is equal to or larger than the prescribed amount of emitted light, the general control unit 70 changes the light emission balance of special light so that the light emission ratios Vs or Bs of violet light V or blue light B is higher than the light emission ratios Gs and Rs of green light G and red light R. At that time, it is preferable that the light emission ratios Vs, Bs, Gs, and Rs corresponding to the respective colors are multiplied by IQLabel determined depending on an image quality mode. For example, since IQLabel is 1 in the high image quality mode, the amount of emitted violet light V or blue light B is not changed. On the other hand, since IQLabel is smaller than 1 in the low image quality mode, the amount of emitted violet light V or blue light B is reduced.

Further, in the special light observation mode, the general control unit 70 increases brightness, which corresponds to green light G or red light R of which the light emission ratio has been reduced with respect to the set light emission balance, through the change of the light emission balance of special light by the first brightness adjustment processing. Specifically, as the first brightness adjustment processing, gain processing for first brightness adjustment is performed on blue signals corresponding to violet light V or blue light B, green signals corresponding to green light G, and red signals corresponding to red light R among the special image signals. In the gain processing for first brightness adjustment, as shown in Equation (3), a gain factor gainG and a gain factor gainR are multiplied by gain correction factors kG (>1) and kRs (>1), respectively. On the other hand, a gain factor gainB is not multiplied by a gain correction factor.

$$gainG^{**} = gainG \times kG$$

$$gainB^{**} = gainB$$

$$gainR^{**} = gainR \times kRs \quad \text{Equation (3)}$$

gainG, gainB, and gainR** denote the gain factors for green signals, blue signals, and red signals having been subjected to the gain processing for first brightness adjustment. Furthermore, it is preferable that the gain correction factor kG is determined on the basis of the amount of reduction in the light emission ratio Gs of green light G with respect to the set light emission balance. Moreover, it is preferable that the gain correction factor kRs is determined on the basis of the amount of reduction in the light emission ratio Rs of red light R with respect to the set light emission balance.

In a case where the image pickup sensor 48 is a frame sequential sensor, processing for adjusting exposure time may be performed as the first brightness adjustment processing. In this case, it is preferable that the exposure time of G-pixels or the exposure time of R-pixels is made to be longer than the exposure time of B-pixels to compensate for a reduction in the amount of green light G or red light R of which the light emission ratio has been reduced with respect to the set light emission balance in a case where light emission balance is changed in the special light observation mode.

It is preferable that the first brightness adjustment processing, that is, the gain processing for first brightness adjustment in the high image quality mode is different from that in the low image quality mode. Specifically, Equation (3) is multiplied by an image quality-correction factor g(IQLabel), which is based on IQLabel determined depending on an image quality mode, and it is preferable that the image quality-correction factor g(IQLabel) in the high image quality mode is different from that in the low image quality mode (see Equation (4)). It is preferable that the image quality-correction factor g(IQLabel) is the reciprocal of IQLabel.

$$gainG^{**} = gainG \times kG \times g(IQLabel)$$

$$gainB^{**} = gainB \times g(IQLabel)$$

$$gainR^{**} = gainR \times kRs \times g(IQLabel) \quad \text{Equation (4)}$$

Figure 4:
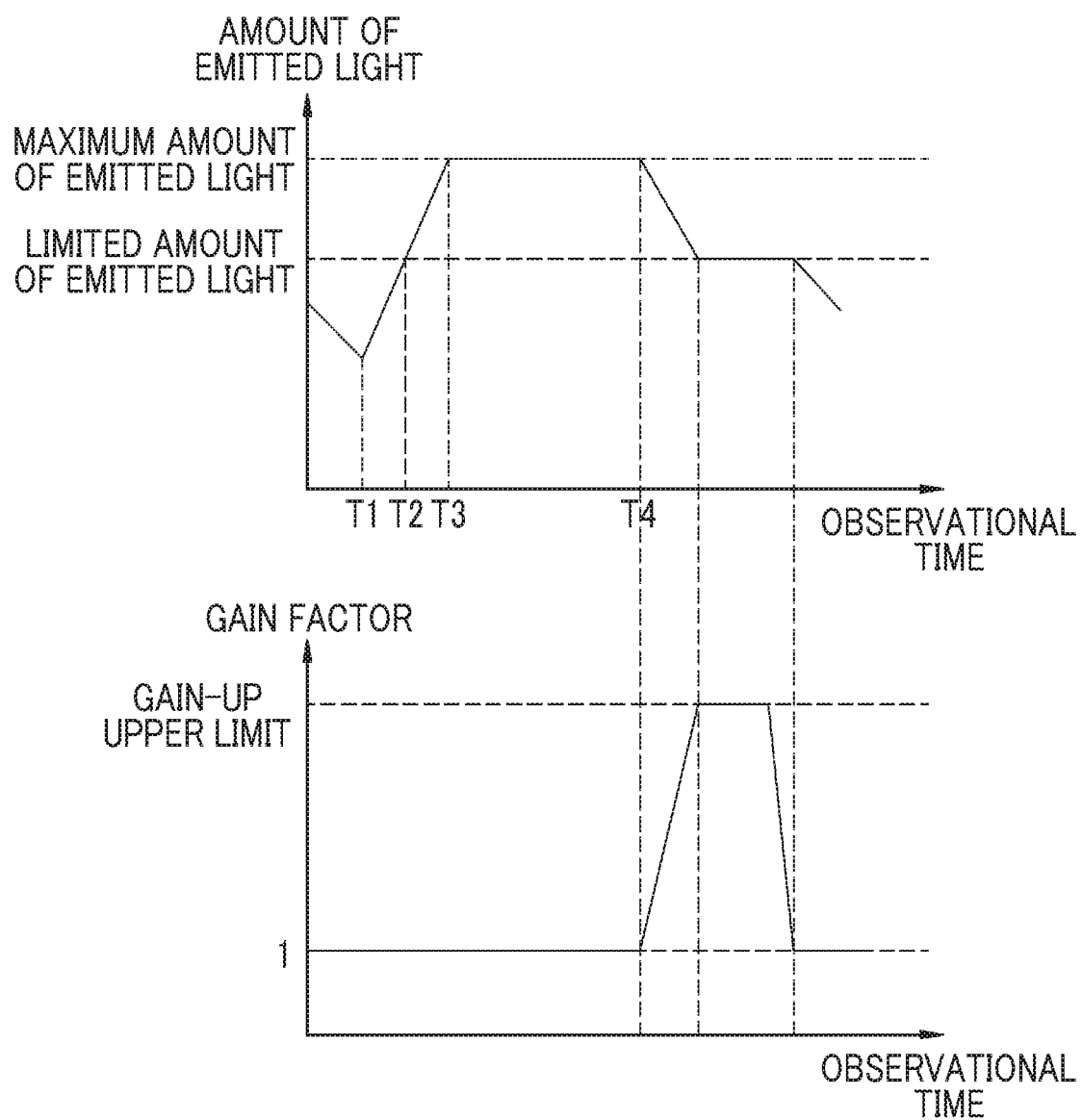
FIG. 4 is a graph showing a relationship between the amount of emitted light and a gain factor in a high image quality mode.

The general control unit 70 performs control to suppress the generation of heat from the distal end part 12d of the endoscope, which is caused by the lengthening of observational time, and to ensure brightness as much as possible according to an image quality mode while suppressing noise. In the high image quality mode, as shown in FIG. 4, the general control unit 70 permits the emission of the amount of emitted normal light or special light up to the maximum amount of emitted light exceeding the limited amount of emitted light in a case where cumulative light emission time (for example, LM×T), which is determined on the basis of the amount LM of emitted light based on normal light or special light and time T having passed from the start of the emission of normal light, does not reach a timing T4 (a threshold value for light emission). Further, in a case where the cumulative light emission time is equal to or shorter than the threshold value for light emission, each of the gain factors gainB, gainG, and gainR to be used in the gain processing is maintained at "1". It is assumed in FIG. 4 that the endoscope is closest to a subject at a timing T1 and then becomes far from the subject.

Figure 5:
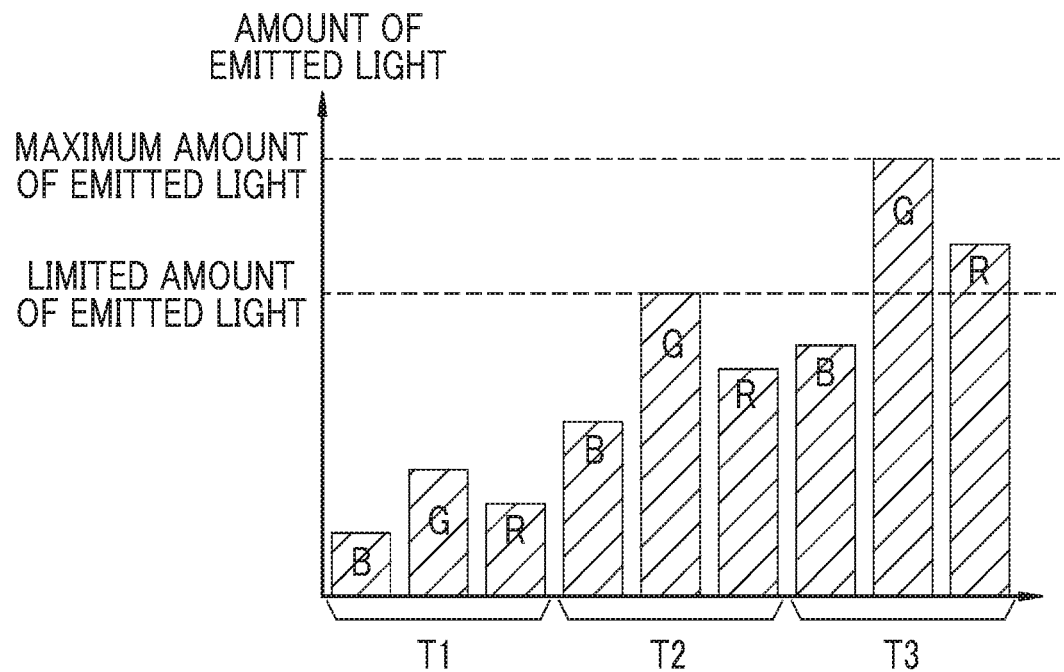
FIG. 5 is a graph showing the amounts of normal light emitted at timings T1, T2, and T3 in the high image quality mode.

For example, as shown in FIG. 5, in the high image quality mode of the normal light observation mode, the amounts of blue light B, green light G, and red light R emitted at the timing T1, the amounts of blue light B, green light G, and red light R emitted at a timing T2 after the timing T1, and the amounts of blue light B, green light G, and red light R emitted at a timing T3 after the timing T2 are increased in a state where light emission balance where the light emission ratio Gc of green light is higher than the light emission ratios Bc and Rc of blue light B and red light is maintained. Further, green light G is emitted at the timings T2 and T3 so that the amount of emitted green light G exceeds the limited amount of emitted light. Only the amount of emitted blue light B is shown in FIG. 5, but the amount of emitted blue light B shown in FIG. 5 may be replaced with the amounts of emitted violet light V and blue light B. The same applies to FIGS. 6, 8, 9, 15, 16, 18, and 19 (it is preferable that "the amount of emitted violet light V is larger than the amount of emitted blue light B" is satisfied in the special light observation mode).

Figure 6:
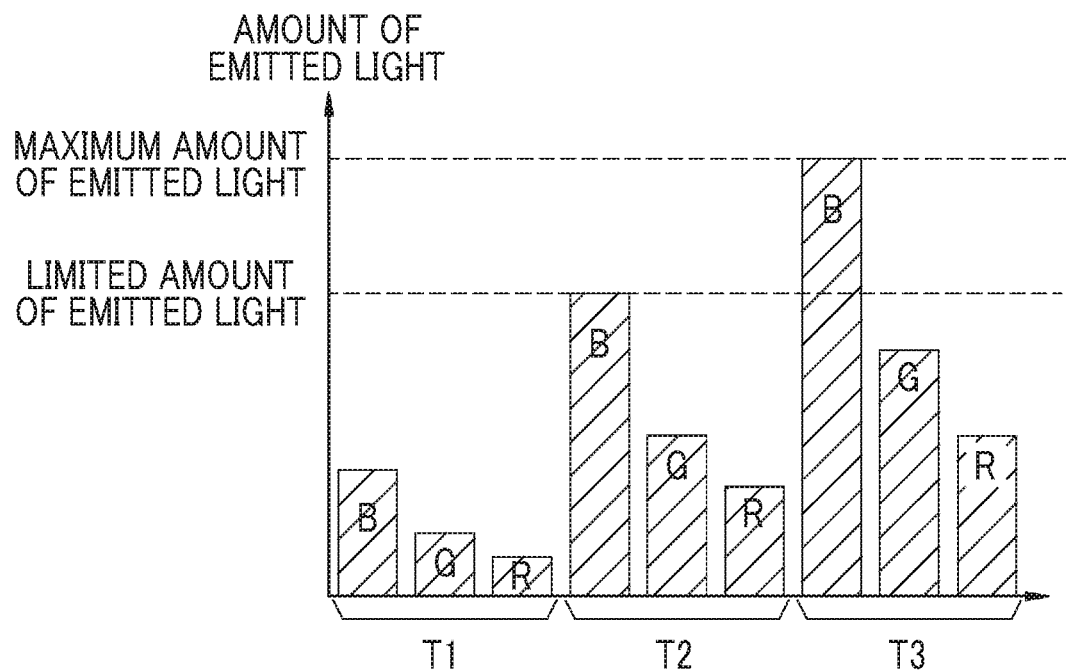
FIG. 6 is a graph showing the amounts of special light emitted at timings T1, T2, and T3 in the high image quality mode.

Furthermore, as shown in FIG. 6, in the high image quality mode of the special light observation mode, the amounts of blue light B, green light G, and red light R emitted at the timing T1, the amounts of blue light B, green light G, and red light R emitted at the timing T2, and the amounts of blue light B, green light G, and red light R emitted at the timing T3 are increased in a state where light emission balance where the light emission ratio Bs of blue light B is higher than the light emission ratios Gs and Rs of green light G and red light R is maintained. Further, blue light B is emitted at the timings T2 and T3 so that the amount of emitted blue light B exceeds the limited amount of emitted light.

On the other hand, in a case where the cumulative light emission time exceeds the timing T4 and the amount of emitted normal light or special light exceeds the limited amount of emitted light, the general control unit 70 reduces the amount of emitted normal light or special light as shown in FIG. 4 and performs third brightness adjustment processing (brightness adjustment processing A), which is used in a case where the amount of emitted light is reduced, on the pixels of the image pickup sensor 48, or the normal image signals or the special image signals. In FIG. 4, after the timing T4, it is assumed that the endoscope is close to a subject and the gain factors gainB, gainG, and gainR return to "1".

Specifically, the general control unit 70 performs gain processing for third brightness adjustment (gain processing for brightness adjustment processing A) on blue signals, green signals, and red signals, which are included in the normal image signals, as the third brightness adjustment processing. In the gain processing for third brightness adjustment, gain-up processing for increasing the gain factors gainB, gainG, and gainR is performed according to a reduction in the amount of emitted light. In the gain-up processing, the gain factors gainB, gainG, and gainR are maintained at a gain-up upper limit for a certain time even after the gain factors gainB, gainG, and gainR reach the gain-up upper limit.

The general control unit 70 may perform processing for adjusting the exposure time of the pixels of the image pickup sensor 48 as the third brightness adjustment processing. In this case, to compensate for a reduction in the amount of emitted light, it is preferable that the exposure time of each pixel of the image pickup sensor 48 after a reduction in the amount of emitted light is made to be longer than the exposure time of each pixel of the image pickup sensor 48 before a reduction in the amount of emitted light.

Figure 7:
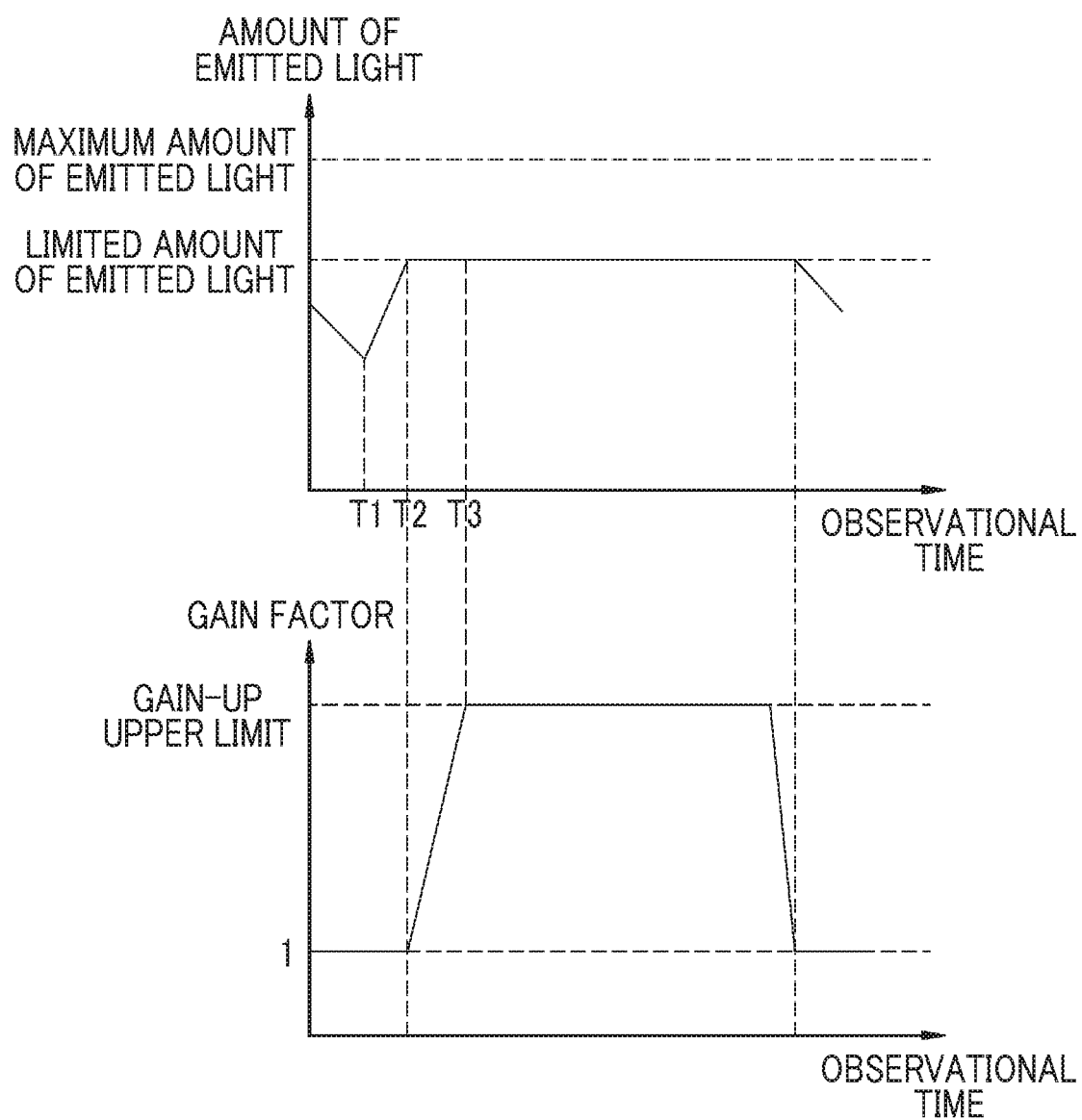
FIG. 7 is a graph showing a relationship between the amount of emitted light and a gain factor in a low high image quality mode.

In the low image quality mode, the general control unit 70 inhibits the emission of light exceeding the limited amount of emitted light regardless of the cumulative light emission time as shown in FIG. 7 in a case where the amount of emitted normal light or special light reaches the limited amount of emitted light. In a case where the amount of emitted normal light or special light is smaller than the limited amount of emitted light, the gain factors gainB, gainG, and gainR to be used in the gain processing are maintained at "1".

Figure 8:
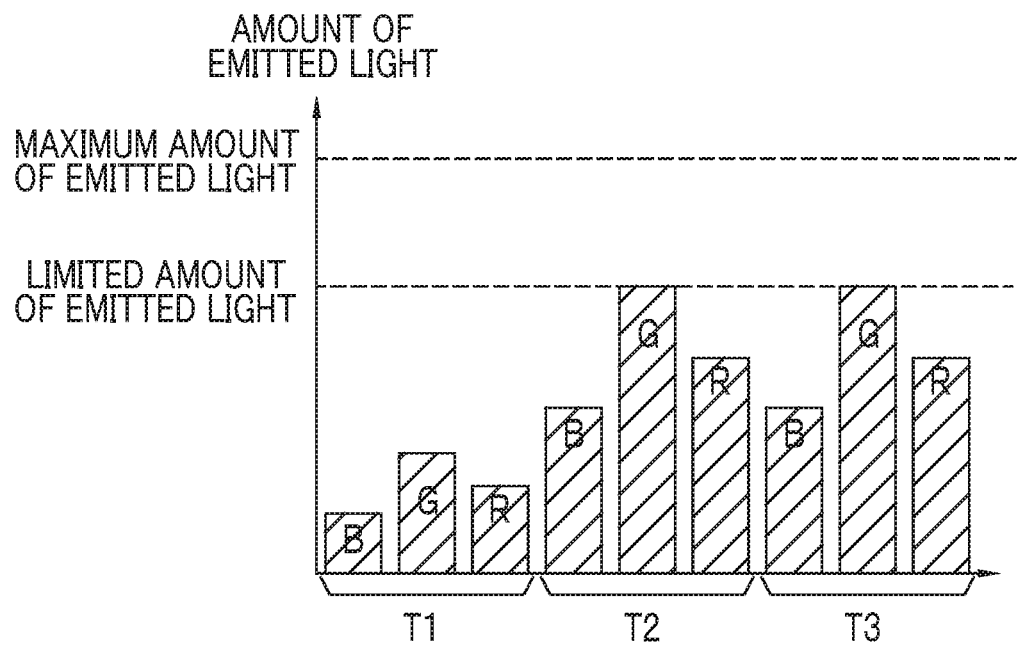
FIG. 8 is a graph showing the amounts of normal light emitted at timings T1, T2, and T3 in the low image quality mode.

For example, as shown in FIG. 8, in the low image quality mode of the normal light observation mode, the amounts of blue light B, green light G, and red light R emitted at the timing T1 and the amounts of blue light B, green light G, and red light R emitted at the timing T2 are increased in a state where light emission balance where the light emission ratio Gc of green light is higher than the light emission ratios Bc and Rc of blue light B and red light is maintained. However, since green light G reaches the limited amount of emitted light at the timing T2, the light emission balance and the amount of emitted light, which are the same as those at the timing T2, are obtained at the timing T3.

Figure 9:
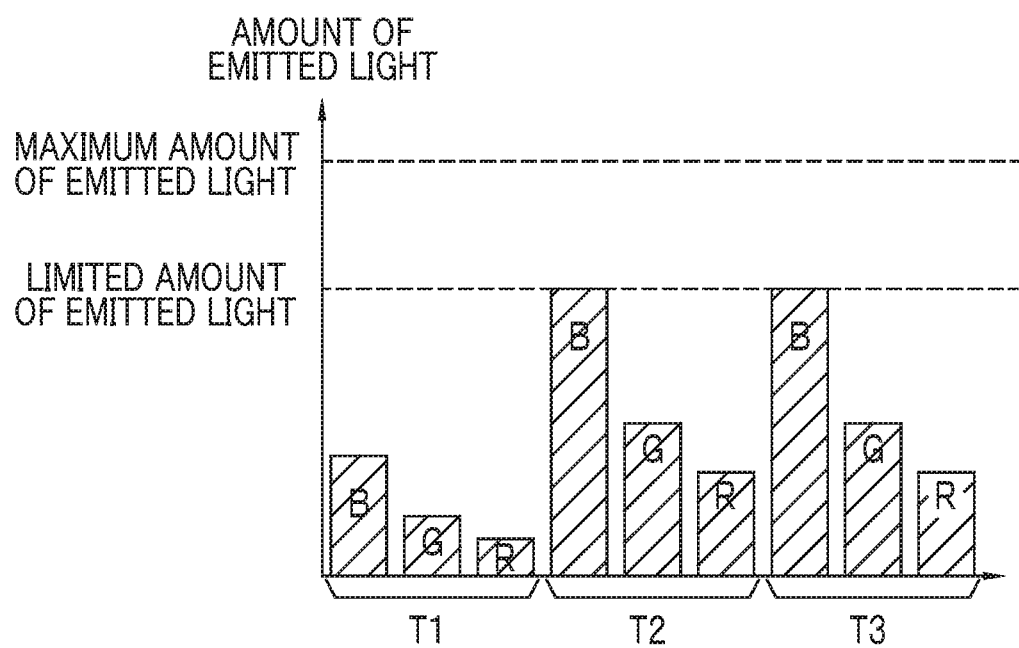
FIG. 9 is a graph showing the amounts of special light emitted at timings T1, T2, and T3 in the low image quality mode.

Further, as shown in FIG. 9, in the low image quality mode of the special light observation mode, the amounts of blue light B, green light G, and red light R emitted at the timing T1 and the amounts of blue light B, green light G, and red light R emitted at the timing T2 are increased in a state where light emission balance where the light emission ratio Bs of blue light B is higher than the light emission ratios Gs and Rs of green light G and red light R is maintained. However, since blue light B reaches the limited amount of emitted light at the timing T2, the light emission balance and the amount of emitted light, which are the same as those at the timing T2, are obtained at the timing T3.

On the other hand, in a case where the amount of emitted normal light or special light reaches the limited amount of emitted light, the general control unit 70 maintains the amount of emitted normal light or special light as shown in FIG. 7 and performs second brightness adjustment processing (brightness adjustment processing B), which is used in a case where the amount of emitted light is maintained, on the pixels of the image pickup sensor 48, or the normal image signals or the special image signals.

Specifically, the general control unit 70 performs gain processing for second brightness adjustment (gain processing for brightness adjustment processing B) on blue signals, green signals, and red signals, which are included in the normal image signals, as the second brightness adjustment processing. In the gain processing for second brightness adjustment, gain-up processing for increasing the gain factors gainB, gainG, and gainR is performed. In the gain-up processing, the gain factors gainB, gainG, and gainR are maintained at a gain-up upper limit for a certain time (from the timing T3 of FIG. 7) even after the gain factors gainB, gainG, and gainR reach the gain-up upper limit.

The general control unit 70 may perform processing for adjusting the exposure time of the pixels of the image pickup sensor 48 as the second brightness adjustment processing. In this case, to ensure brightness, it is preferable that the exposure time of each pixel of the image pickup sensor 48 after the maintaining of the amount of emitted light is made to be longer than the exposure time of each pixel of the image pickup sensor 48 before the maintaining of the amount of emitted light.

It is preferable that the limited amount of emitted light is determined on the basis of the gain-up upper limit of the gain-up processing. For example, in a case where the gain-up upper limit is "1.4", the limited amount of emitted light becomes "1/1.4" ($\approx$71(%)) considering that the lower limit of a gain is "1". Further, since the amount of noise is also increased as the gain factor is increased, it is preferable that the gain-up upper limit is determined in consideration of a level where deterioration caused by noise can be allowed. It is preferable that the level where deterioration can be allowed is obtained on the basis of a value to be obtained in a case where a picture quality scale (PQS) (M. Miyahara, Objective picture quality scale (PQS) for image coding, IEEE transactions on communications, vol 46, Issue9, September 1998), which has a high correlation with a subjective evaluation value, is applied to the image of a subject obtained from the image pickup of a gray or color patch. Furthermore, to avoid a case where distant structures are not seen due to noise, it is preferable that the spatial resolution of an image is not changed under a situation where noise is allowed.

Figure 10:
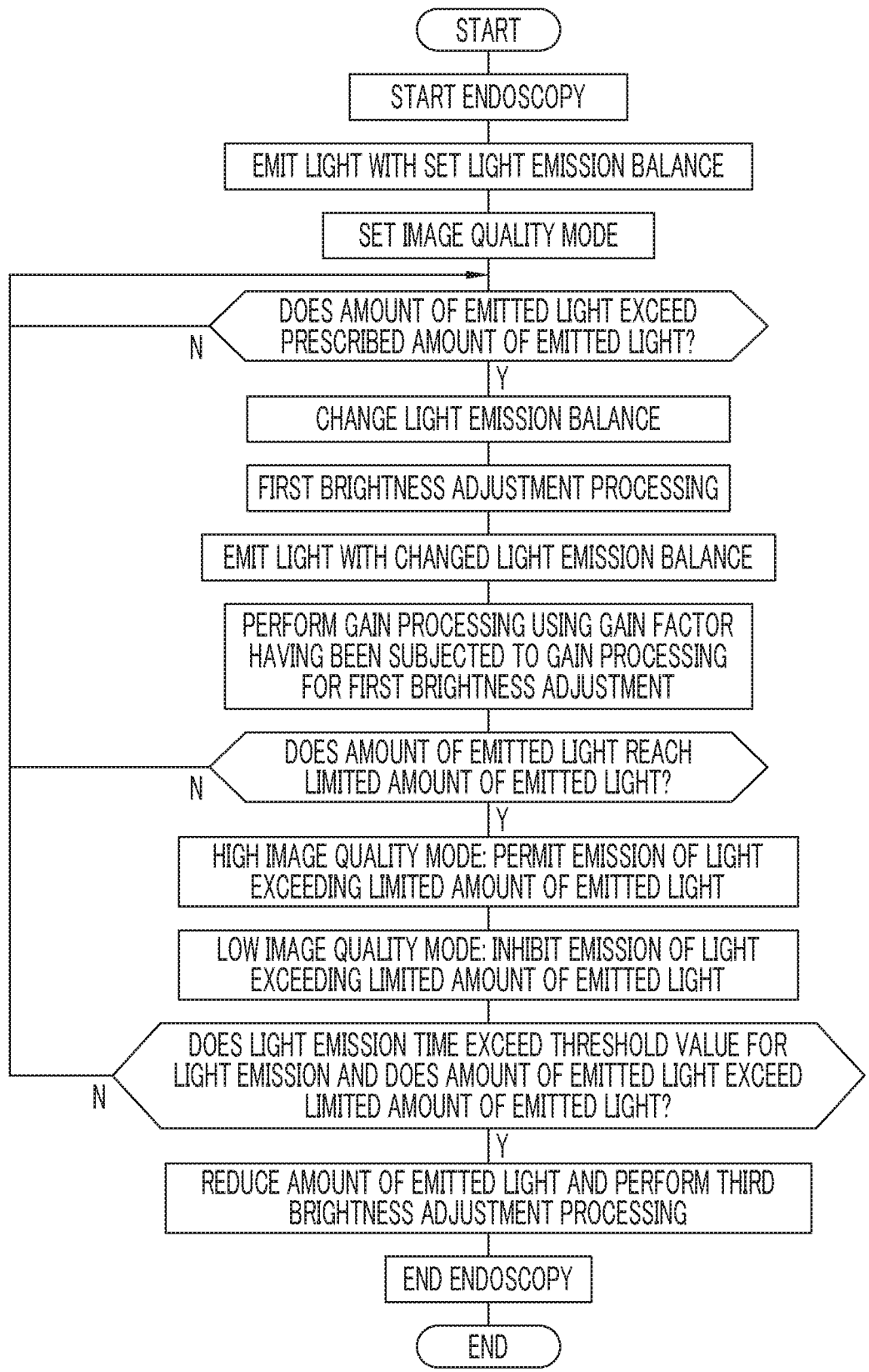
FIG. 10 is a flowchart showing a series of flows of the invention.

Next, a series of flows of the invention will be described with reference to a flowchart shown in FIG. 10. The endoscope system 10 starts to be driven with the start of an endoscopy. Accordingly, in a case where the light source device 14 is driven, normal light or special light is emitted with the set light emission balance. That is, normal light of which the light emission balance of violet light V, blue light B, green light G, and red light R corresponds to Vc:Bc:Gc:Rc or special light of which the light emission balance of violet light V, blue light B, green light G, and red light R corresponds to Vs:Bs:Gs:Rs starts to be emitted. Further, an image quality mode is set by the user interface 19. IQLabel is set to "1" in a case where an image quality mode is the high image quality mode, and IQLabel is set to "1" or less in a case where an image quality mode is the low image quality mode.

In a case where the amount of emitted normal light or special light is smaller than the prescribed amount of emitted light, the normal light or the special light is emitted with the set light emission balance. In this case, the gain factors gainB, gainG, and gainR to be used in the gain processing are maintained at "1". On the other hand, in a case where the amount of emitted normal light or special light is equal to or larger than the prescribed amount of emitted light, the general control unit 70 changes the set light emission balance and performs the first brightness adjustment processing on the pixels of the image pickup sensor 48, or the normal image signals or the special image signals to increase brightness, which corresponds to light of which the light emission ratio has been reduced, through the change of light emission balance. At the time of magnification observation, there is a possibility that the contrast of blood vessels may be changed in a case where light emission balance is changed. For this reason, it is preferable that light emission balance is changed at the time of only during non-magnification observation and light emission balance is not changed at the time of magnification observation.

For example, in the normal light observation mode, the light emission ratio Gc of green light G is made to be higher than the light emission ratios Vc, Bc, and Rc of violet light V, blue light B, and red light R with respect to the set light emission balance. According to this, as the first brightness adjustment processing, the gain processing for first brightness adjustment is performed on blue signals, green signals, and red signals of the normal image signals to compensate for a reduction in brightness that is caused by a reduction in the light emission ratios Vc, Bc, and Rc of violet light V, blue light B, and red light R. The gain factors gainB*, gainG*, and gainR* having been subjected to the gain processing for first brightness adjustment are obtained from the gain processing for first brightness adjustment.

Further, in the special light observation mode, the light emission ratios Vs and Bs of violet light V and blue light B are made to be higher than the light emission ratios Gs and Rs of green lights G and red light R with respect to the set light emission balance. According to this, as the first brightness adjustment processing, the gain processing for first brightness adjustment is performed on blue signals, green signals, and red signals of the special image signals to compensate for a reduction in brightness that is caused by a reduction in the light emission ratios Gs and Rs of green light G and red light R. The gain factors gainB, gainG, and gainR** having been subjected to the gain processing for first brightness adjustment are obtained from the gain processing for first brightness adjustment.

In a case where the change of light emission balance and the gain processing for first brightness adjustment are completed as described above, normal light or special light is emitted with the changed light emission balance. Furthermore, the gain factors gainB*, gainG*, and gainR* or the gain factors gainB, gainG, and gainR** having been subjected to the gain processing for first brightness adjustment are used for normal image signals or special image signals, which are obtained on the basis of normal light or special light having the changed light emission balance, in the gain processing.

Further, in a case where the amount of emitted normal light or special light reaches the limited amount of emitted light, the general control unit 70 permits the emission of normal light or special light exceeding the limited amount of emitted light in the high image quality mode but the general control unit 70 inhibits the emission of normal light or special light exceeding the limited amount of emitted light and maintains the amount of emitted normal light or special light at the limited amount of emitted light in the low image quality mode. In this case, in the low image quality mode, the general control unit 70 performs the second brightness adjustment processing on the pixels of the image pickup sensor 48, or the normal image signals or the special image signals to ensure brightness even though the amount of emitted normal light or special light is maintained within the limited amount of emitted light.

Furthermore, in a case where cumulative light emission time exceeds the threshold value for light emission and the amount of emitted normal light or special light exceeds the limited amount of emitted light, the general control unit 70 reduces the amount of emitted normal light or special light. In this case, the general control unit 70 performs the third brightness adjustment processing on the pixels of the image pickup sensor 48, or the normal image signals or the special image signals to compensate for a reduction in brightness that is caused by a reduction in the amount of emitted normal light or special light.

The above-mentioned series of processing and the like are repeatedly performed until an endoscopy ends.

An image quality mode has been manually set using the user interface 19 in the first embodiment, but an image quality mode may be automatically switched using information about the movement of the distal end part 12d of the endoscope. For example, in a case where the distal end part 12d of the endoscope is being moved significantly, there is a possibility that a situation where brightness is considered to be more important than image quality may be made since there is a possibility that the screening, such as pickup, of a lesion part or the like may be being performed. Under such a situation, it is preferable that an image quality mode is switched to the low image quality mode in a case where the amount of movement of the distal end part 12d of the endoscope is equal to or larger than a threshold value for the amount of movement. On the other hand, in a case where the distal end part 12d of the endoscope is being moved not so significantly, there is a possibility that a situation where priority is given to image quality may be made since there is a possibility that the complete examination of an object to be observed may be being performed. Under such a situation, it is preferable that an image quality mode is switched to the high image quality mode in a case where the amount of movement of the distal end part 12d of the endoscope is equal to or larger than a threshold value for the amount of movement. The amount of movement of the distal end part 12d of the endoscope may be measured by, for example, an acceleration sensor (not shown) provided in the distal end part 12d, or may be obtained from a difference image between a plurality of image signals of which image pickup timings are different (for example, a difference value of the difference image is small in a case where the amount of movement is small).

Second Embodiment

In a second embodiment, the general control unit 70 performs control to suppress the generation of heat from the distal end part 12d of the endoscope according to the type of the endoscope 12 connected to the endoscope connection unit.

Figure 11:
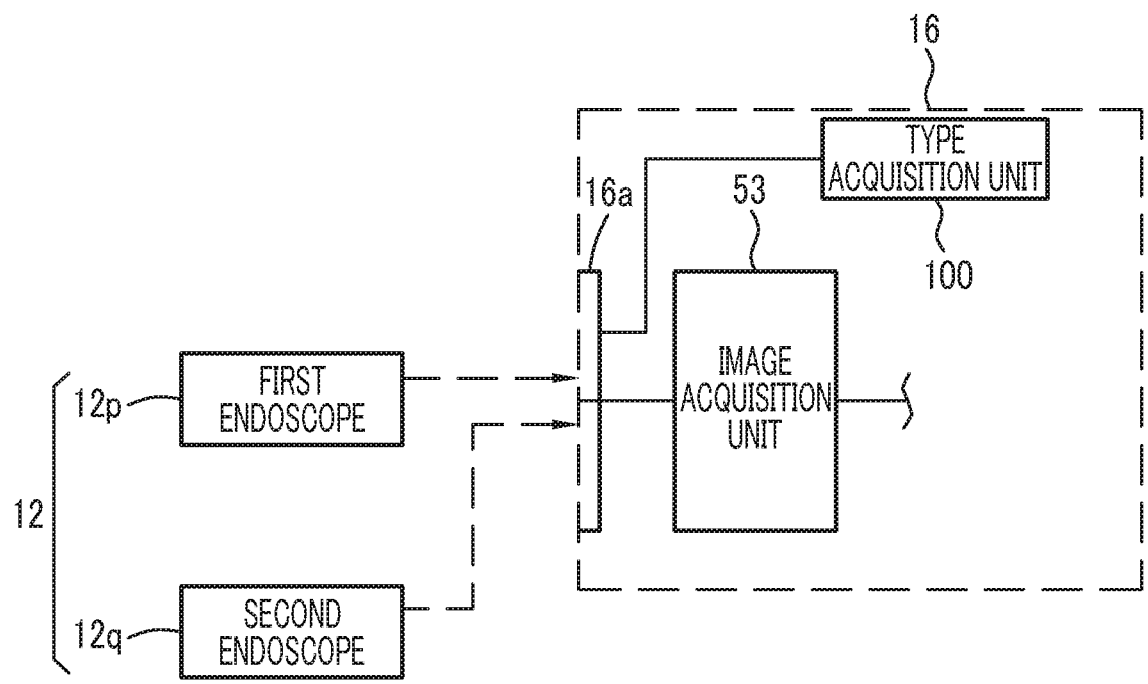
FIG. 11 is a block diagram of a processor device of a second embodiment.

In the second embodiment, as shown in FIG. 11, the processor device 16 comprises a type acquisition unit 100 that determines the type of the endoscope 12 connected to the processor-side connection unit 16a serving as the endoscope connection unit. The endoscope 12, which can be connected to the endoscope connection unit, includes a first endoscope 12p and a second endoscope 12q of which the types, such as diameters of distal end parts 12d, are different from each other. In the second embodiment, the type acquisition unit 100 determines whether the endoscope 12 connected to the processor-side connection unit 16a is the first endoscope 12p or the second endoscope 12q. An endoscope system according to the second embodiment is substantially the same as the endoscope system according to the first embodiment except that the type acquisition unit 100 is added.

In the second embodiment, a light source control unit 21 performs control to make the wavelength balance of light in the respective wavelength ranges, which is obtained in a case where the type of the endoscope corresponds to the first endoscope 12p, and the wavelength balance of light in the respective wavelength ranges, which is obtained in a case where the type of the endoscope corresponds to the second endoscope 12q, be different from each other. Specifically, in the normal light observation mode, as shown in (A) and (B) of FIG. 12, the light source control unit makes the light emission ratio of violet light V, blue light B, or red light R, which is obtained in a case where the type of the endoscope corresponds to the first endoscope 12p, be higher than the light emission ratio of violet light V, blue light B, or red light R that is obtained in a case where the type of the endoscope corresponds to the second endoscope. On the other hand, in the special light observation mode, as shown in (A) and (B) of FIG. 13, the light source control unit makes the light emission ratio of green light G or red light R, which is obtained in a case where the type of the endoscope corresponds to the first endoscope 12p, be higher than the light emission ratio of green light G or red light R that is obtained in a case where the type of the endoscope corresponds to the second endoscope 12q.

Since light emission balance is controlled as described above, it is possible to make the generation of heat be difficult by making the light emission ratio in the case of the second endoscope 12q be lower than the light emission ratio in the case of the first endoscope 12p in a case where it is difficult to release heat since the second endoscope 12q is a small-diameter endoscope of which the diameter of an distal end part 12d is small. In a case where the light emission ratio is made low, it is preferable that brightness is increased by brightness adjustment processing, such as gain processing, so that color balance is not changed before and after a change in the light emission ratio.

The first endoscope 12p is, for example, a large-diameter endoscope of which the diameter of a distal end part 12d is larger than the diameter of the distal end part 12d of the second endoscope 12q. The second endoscope 12q is, for example, a small-diameter endoscope of which the diameter of the distal end part 12d is smaller than the diameter of the distal end part 12d of the first endoscope 12p. Since there is a possibility that it is easy to release heat from the distal end part 12d in the case of a large-diameter endoscope as compared to the case of a small-diameter endoscope, the general control unit 70 may permit the emission of the amount of emitted light exceeding the limited amount of emitted light. On the other hand, since there is a possibility that it is difficult to release heat from the distal end part 12d in the case of a small-diameter endoscope as compared to the case of a large-diameter endoscope, it is preferable that the amount of emitted light is suppressed within the limited amount of emitted light.

The first endoscope 12p is, for example, a magnifying endoscope comprising a magnification optical system (not shown), which is used to magnify or reduce an object to be observed in size, in a distal end part 12d thereof. The second endoscope 12q is, for example, a non-magnifying endoscope not comprising a magnification optical system in a distal end part 12d thereof. Since there is a possibility that the complete examination of an object to be observed may be performed using the magnification optical system in the case of the magnifying endoscope, it is preferable that an image is acquired with a high image quality in the case of the magnifying endoscope. On the other hand, since there is a possibility that the screening, such as pickup, of a lesion part may be mainly performed and the complete examination of an object to be observed may not be performed in the case of the non-magnifying endoscope, it is preferable that an observation may be made with a low image quality while priority is given to brightness in the case of the non-magnifying endoscope.

Further, in the second embodiment, the general control unit 70 performs control to suppress the generation of heat from the distal end part 12d of the endoscope, which is caused by the lengthening of observational time, and to ensure brightness as much as possible according to the type of the endoscope 12 while suppressing noise. As shown in FIG. 14, the general control unit 70 permits the emission of the amount of emitted normal light or special light up to the maximum amount of emitted light exceeding the limited amount of emitted light in a case where the type of the endoscope corresponds to the first endoscope 12p and cumulative light emission time (for example, LMxT) does not reach a timing T4 (a threshold value for light emission). Further, in a case where the cumulative light emission time is equal to or shorter than the threshold value for light emission, each of the gain factors gainB, gainG, and gainR to be used in the gain processing is maintained at "1".

For example, as shown in FIG. 15, in the normal light observation mode in a case where the type of the endoscope corresponds to the first endoscope 12p, the amounts of blue light B, green light G, and red light R emitted at the timing T1, the amounts of blue light B, green light G, and red light R emitted at the timing T2, and the amounts of blue light B, green light G, and red light R emitted at the timing T3 are increased in a state where light emission balance where the light emission ratio Gc of green light is higher than the light emission ratios Bc and Rc of blue light B and red light is maintained. Further, green light G is emitted at the timings T2 and T3 so that the amount of emitted green light G exceeds the limited amount of emitted light.

Furthermore, as shown in FIG. 16, in the special light observation mode in a case where the type of the endoscope corresponds to the first endoscope 12p, the amounts of blue light B, green light G, and red light R emitted at the timing T1, the amounts of blue light B, green light G, and red light R emitted at the timing T2, and the amounts of blue light B, green light G, and red light R emitted at the timing T3 are increased in a state where light emission balance where the light emission ratio Bs of blue light B is higher than the light emission ratios Gs and Rs of green light G and red light R is maintained. Further, blue light B is emitted at the timings T2 and T3 so that the amount of emitted blue light B exceeds the limited amount of emitted light.

On the other hand, in a case where the cumulative light emission time exceeds the timing T4 and the amount of emitted normal light or special light exceeds the limited amount of emitted light, the general control unit 70 reduces the amount of emitted normal light or special light as shown in FIG. 14 and performs third brightness adjustment processing, which is used in a case where the amount of emitted light is reduced, on the pixels of the image pickup sensor 48, or the normal image signals or the special image signals. It is preferable that the third brightness adjustment processing increases brightness according to a reduction in the amount of emitted light.

Specifically, the general control unit 70 performs gain processing for third brightness adjustment on blue signals, green signals, and red signals, which are included in the normal image signals, as the third brightness adjustment processing. In the gain processing for third brightness adjustment, gain-up processing for increasing the gain factors gainB, gainG, and gainR is performed according to a reduction in the amount of emitted light. In the gain-up processing, the gain factors gainB, gainG, and gainR are maintained at a gain-up upper limit for a certain time even after the gain factors gainB, gainG, and gainR reach the gain-up upper limit.

The general control unit 70 may perform processing for adjusting the exposure time of the pixels of the image pickup sensor 48 as the third brightness adjustment processing. In this case, to compensate for a reduction in the amount of emitted light, it is preferable that the exposure time of each pixel of the image pickup sensor 48 after a reduction in the amount of emitted light is made to be longer than the exposure time of each pixel of the image pickup sensor 48 before a reduction in the amount of emitted light.

In a case where the type of the endoscope corresponds to the second endoscope 12q, the general control unit 70 inhibits the emission of light exceeding the limited amount of emitted light regardless of the cumulative light emission time as shown in FIG. 17 in a case where the amount of emitted normal light or special light reaches the limited amount of emitted light. In a case where the amount of emitted normal light or special light is smaller than the limited amount of emitted light, the gain factors gainB, gainG, and gainR to be used in the gain processing are maintained at "1".

For example, as shown in FIG. 18, in the normal light observation mode in a case where the type of the endoscope corresponds to the second endoscope 12q, the amounts of blue light B, green light G, and red light R emitted at the timing T1 and the amounts of blue light B, green light G, and red light R emitted at the timing T2 are increased in a state where light emission balance where the light emission ratio Gc of green light is higher than the light emission ratios Bc and Rc of blue light B and red light R is maintained. However, since green light G reaches the limited amount of emitted light at the timing T2, the light emission balance and the amount of emitted light, which are the same as those at the timing T2, are obtained at the timing T3. Further, the light emission ratios Bc and Rc of blue light B and red light R, which are obtained in a case where the type of the endoscope corresponds to the second endoscope 12q, are lower than the light emission ratios Bc and Rc of blue light B and red light R that are obtained in a case where the type of the endoscope corresponds to the first endoscope 12p (see FIG. 15).

Further, as shown in FIG. 19, in the special light observation mode in a case where the type of the endoscope corresponds to the second endoscope 12q, the amounts of blue light B, green light G, and red light R emitted at the timing T1 and the amounts of blue light B, green light G, and red light R emitted at the timing T2 are increased in a state where light emission balance where the light emission ratio Bs of blue light B is higher than the light emission ratios Gs and Rs of green light G and red light R is maintained. However, since blue light B reaches the limited amount of emitted light at the timing T2, the light emission balance and the amount of emitted light, which are the same as those at the timing T2, are obtained at the timing T3. Furthermore, the light emission ratios Bs and Rs of blue light B and red light R, which are obtained in a case where the type of the endoscope corresponds to the second endoscope 12q, are lower than the light emission ratios Bs and Rs of blue light B and red light R that are obtained in a case where the type of the endoscope corresponds to the first endoscope 12p (see FIG. 16).

On the other hand, in a case where the amount of emitted normal light or special light reaches the limited amount of emitted light, the general control unit 70 maintains the amount of emitted normal light or special light as shown in FIG. 17 and performs second brightness adjustment processing, which is used in a case where the amount of emitted light is maintained, on the pixels of the image pickup sensor 48, or the normal image signals or the special image signals.

Specifically, the general control unit 70 performs gain processing for second brightness adjustment on blue signals, green signals, and red signals, which are included in the normal image signals, as the second brightness adjustment processing. In the gain processing for second brightness adjustment, gain-up processing for increasing the gain factors gainB, gainG, and gainR is performed. In the gain-up processing, the gain factors gainB, gainG, and gainR are maintained at a gain-up upper limit for a certain time even after the gain factors gainB, gainG, and gainR reach the gain-up upper limit.

The general control unit 70 may perform processing for adjusting the exposure time of the pixels of the image pickup sensor 48 as the second brightness adjustment processing. In this case, to ensure brightness, it is preferable that the exposure time of each pixel of the image pickup sensor 48 after the maintaining of the amount of emitted light is made to be longer than the exposure time of each pixel of the image pickup sensor 48 before the maintaining of the amount of emitted light.

In the first and second embodiments, the brightness of the normal observation image or the special observation image has been adjusted by the gain processing or the adjustment of the exposure time of the pixels of the image pickup sensor 48 as the first brightness adjustment processing, the second brightness adjustment processing, or the third brightness adjustment processing. However, the brightness of the normal observation image or the special observation image may be adjusted by other methods. For example, binning for adding a plurality of pixels as one pixel may be performed as the first brightness adjustment processing, the second brightness adjustment processing, or the third brightness adjustment processing. However, in this case, it is preferable that the level of binning (the number of pixels to be added, or the like) is set in consideration of the level of allowable spatial resolution since spatial resolution is lowered due to binning.

Pieces of light, which have the light emission spectra shown in FIG. 3 and four colors, have been used in the first and second embodiments, but light emission spectra do not need to be limited to the light emission spectrum shown in FIG. 3. For example, one piece of color light, which has a continuous light emission spectrum over the wavelength range between green light R and red light R, may be used as green light G and red light R.

The hardware structures of the processing units, which are included in the processor device 16 in the first and second embodiments, such as the image acquisition unit 53, the brightness information-calculation unit 54, the DSP 56, the gain processing unit 56a, the noise removing unit 58, the signal switching unit 60, the normal observation image-processing unit 62, the special observation image-processing unit 63, the static image storage unit 67, the display control unit 66, the static image-storage-control unit 68, and the general control unit 70, are various processors to be described below. The various processors include: a central processing unit (CPU) that is a general-purpose processor functioning as various processing units by executing software (program); a programmable logic device (PLD) that is a processor of which circuit configuration can be changed after manufacture, such as a field programmable gate array (FPGA); a graphical processing unit (GPU); a dedicated electrical circuit that is a processor having circuit configuration designed exclusively to perform various kinds of processing; and the like.

One processing unit may be formed of one of these various processors, or may be formed of a combination of two or more same kind or different kinds of processors (for example, a plurality of FPGAs, a combination of a CPU and an FPGA, or a combination of a CPU and a GPU). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined.

The invention can be applied to various medical image processing devices other than the processor device that is to be combined with the endoscope systems described in the first and second embodiments.

EXPLANATION OF REFERENCES

10: endoscope system
12: endoscope
12a: insertion part
12b: operation part
12c: bendable part
12d: distal end part
12e: angle knob
12p: first endoscope
12q: second endoscope
13a: mode changeover switch
13b: static image-acquisition instruction unit
14: light source device
14a: light source-side connection unit
16: processor device
16a: processor-side connection unit
18: monitor
19: user interface
20: light source unit
20a: V-LED
20b: B-LED
20c: G-LED
20d: R-LED
21: light source control unit
23: optical path-combination unit
30a: illumination optical system
30b: image pickup optical system
41: light guide
45: illumination lens
46: objective lens
48: image pickup sensor
49: image pickup control unit
50: CDS/AGC circuit
53: image acquisition unit
54: brightness information-calculation unit
56: DSP
56a: gain processing unit
58: noise removing unit
60: signal switching unit
62: normal observation image-processing unit
63: special observation image-processing unit
66: display control unit
67: static image storage unit
68: static image-storage-control unit
70: general control unit
100: type acquisition unit
T1, T2, T3: timing

What is claimed is:

1. An endoscope system comprising:
a light source that emits light in a plurality of wavelength ranges and is capable of changing a light emission ratio for a respective wavelength range of the plurality of wavelength ranges;
an endoscope that includes an image pickup sensor picking up an image of an object to be observed illuminated with the light in the respective wavelength range; and
a processor configured to:
acquire image signals obtained from the image pickup of the object to be observed;
determine whether a type of the endoscope connected to an endoscope connection unit is a first endoscope or a second endoscope; and
control the light source to control a light emission balance for the respective wavelength range of the plurality of wavelength ranges, the first endoscope and the second endoscope being applicable to a normal light observation mode and a special light observation mode, which are different from each other in the light emission balance, wherein
in response to determining that the type of the endoscope connected to the endoscope connection unit is the first endoscope, the processor changes the light emission balance to a first light emission balance corresponding to the first endoscope,
in response to determining that the type of the endoscope connected to the endoscope connection unit is the second endoscope, the processor changes the light emission balance to a second light emission balance corresponding to the second endoscope, the first light emission balance and the second light emission balance being different at least in the normal light observation mode, and
the processor is further configured to
permit light emission of an amount of emitted light up to a maximum amount of emitted light exceeding a limited amount of emitted light, until a cumulative light emission time, which is determined on a basis of amounts of emitted light in the respective wavelength range and a time having passed from a start of emission of the light in the respective wavelength range, reaches a threshold value for the light emission in the use of the first endoscope; and
inhibit emission of light exceeding the limited amount of emitted light regardless of the cumulative light emission time, after an amount of emitted light in at least one wavelength range of the light in the respective wavelength range reaches the limited amount of emitted light in the use of the second endoscope.

2. The endoscope system according to claim 1, wherein the light in the respective wavelength range includes light in a short wavelength range, green light, or red light, and
the processor performs at least any one of
making a light emission ratio of the light in the short wavelength range or the red light for the first endoscope be higher than a light emission ratio of the light in the short wavelength range or the red light for the second endoscope, in the normal light observation mode, or
making a light emission ratio of the green light or the red light for the first endoscope be higher than a light emission ratio of the green light or the red light for the second endoscope, in the special light observation mode.

3. The endoscope system according to claim 1, wherein the processor is further configured to
reduce amounts of emitted light in the respective wavelength range and apply a first brightness adjustment processing, which is used upon the amounts of emitted light being reduced, on pixels of the image pickup sensor or the image signals, in response to the first endoscope being used; a cumulative light emission time, which is determined on the basis of the amounts of emitted light in the respective wavelength range and time having passed from a start of emission of the light in the respective wavelength range, exceeding a threshold value for light emission; and the amount of emitted light in at least one wavelength range of the light in the respective wavelength range exceeding a limited amount of emitted light; and
maintain the amounts of emitted light in the respective wavelength range and perform a second brightness adjustment processing, which is used upon the amounts of emitted light being maintained, on a pixel of the image pickup sensor or the image signals, in response to the second endoscope being used and the amount of emitted light in at least one wavelength range of the light in the respective wavelength range reaching the limited amount of emitted light.

4. The endoscope system according to claim 3, wherein the first brightness adjustment processing increases brightness according to a reduction in the amount of emitted light.

5. The endoscope system according to claim 3, wherein the first brightness adjustment processing is gain processing for the first brightness adjustment processing, and the limited amount of emitted light is determined on a basis of a gain-up upper limit for the gain processing for the first brightness adjustment processing, and
the second brightness adjustment processing is gain processing for the second brightness adjustment processing, and the limited amount of emitted light is determined on a basis of a gain-up upper limit for the gain processing for the second brightness adjustment processing.

6. The endoscope system according to claim 1, wherein a diameter of a distal end part of the first endoscope is larger than a diameter of a distal end part of the second endoscope.

7. The endoscope system according to claim 1, wherein the first endoscope is a magnifying endoscope and the second endoscope is a non-magnifying endoscope.

* * * * *